(12) United States Patent
FitzGerald

(10) Patent No.: US 7,314,625 B2
(45) Date of Patent: Jan. 1, 2008

(54) **CHIMERIC PROTEIN COMPRISING NON-TOXIC *PSEUDOMONAS* EXOTOXIN A AND TYPE IV PILIN SEQUENCES**

(75) Inventor: David J. FitzGerald, Rockville, MD (US)

(73) Assignee: The United States as represented by the Secretary of the Department of Health and Human Services, Washington, DC (US)

( * ) Notice: Subject to any disclaimer, the term of this patent is extended or adjusted under 35 U.S.C. 154(b) by 332 days.

(21) Appl. No.: 10/432,412

(22) PCT Filed: Dec. 20, 2001

(86) PCT No.: PCT/US01/49143

§ 371 (c)(1),
(2), (4) Date: May 21, 2003

(87) PCT Pub. No.: WO02/060935

PCT Pub. Date: Aug. 8, 2002

(65) Prior Publication Data

US 2004/0071731 A1    Apr. 15, 2004

Related U.S. Application Data

(60) Provisional application No. 60/257,877, filed on Dec. 21, 2000.

(51) Int. Cl.
*A61K 39/02* (2006.01)
*C12N 15/09* (2006.01)
*C07K 14/00* (2006.01)

(52) U.S. Cl. .............. 424/192.1; 424/190.1; 424/242.1; 435/69.3; 435/252.3; 435/253.3; 435/320.1; 530/350; 536/23.7

(58) Field of Classification Search .............. 424/190.1, 424/242.1, 192.1; 435/69.3, 252.3, 253.3, 435/320.1; 530/350; 536/23.7
See application file for complete search history.

(56) References Cited

U.S. PATENT DOCUMENTS

| 4,892,827 A | 1/1990 | Pastan et al. |
|---|---|---|
| 5,082,927 A | 1/1992 | Pastan et al. |
| 5,328,984 A | 7/1994 | Pastan et al. |
| 5,458,878 A | 10/1995 | Pastan et al. |
| 5,512,658 A | 4/1996 | Pastan et al. |
| 5,573,916 A | 11/1996 | Cheronis et al. |
| 5,602,095 A | 2/1997 | Pastan et al. |
| 5,696,237 A | 12/1997 | Fitzgerald et al. |
| 5,705,156 A | 1/1998 | Pastan et al. |
| 5,705,163 A | 1/1998 | Pastan et al. |
| 5,854,044 A | 12/1998 | Pastan et al. |
| 5,863,745 A | 1/1999 | Fitzgerald et al. |
| 5,965,406 A | 10/1999 | Murphy |
| 5,980,895 A | 11/1999 | Pastan et al. |
| 6,011,002 A | 1/2000 | Pastan et al. |
| 6,022,950 A | 2/2000 | Murphy |
| 6,074,644 A | 6/2000 | Pastan et al. |
| 6,086,900 A | 7/2000 | Draper |
| 6,426,075 B1 | 7/2002 | Fitzgerald et al. |
| 6,498,233 B1 | 12/2002 | Wels et al. |

FOREIGN PATENT DOCUMENTS

| EP | 0 439 954 A2 | 8/1991 |
|---|---|---|
| WO | WO90/13563 | 11/1990 |
| WO | WO93/11791 | 6/1993 |
| WO | WO95/31483 | 11/1995 |
| WO | WO97/13529 A1 | 4/1997 |
| WO | WO98/20135 A2 | 5/1998 |
| WO | WO99/02712 A1 | 1/1999 |
| WO | WO99/57142 | 11/1999 |

OTHER PUBLICATIONS

Fitzgerald, D. et al., "Characterization of V3 Loop-Pseudomonas Exotoxin Chimeras" J. Biol. Chem. 273(16):9951-9958 (1998).
Hahn, H. et al., "Pilin-Based Anti-Pseudomonas Vaccines: Latest Developments and Perspectives" Behring Institute: Mitteilungen, Marburg, DE 98:315-325 (1997).
Hertle, R. et al., "Dual-Function Vaccine for *Pseudomonas aeruginosa*: Characterization of Chimeric Exotoxin A-Pilin Protein" Infection and Immunity 69(11):6962-6969 (2001).
Lukac, M. et al., "Toxoid of *Pseudomonas aeruginosa* Exotoxin A Generated by Deletion of an Active-Site Residue" Infection and Immunity 56(12):3095-3098 (1988).
Wall, D. and Kaiser, D., " Type IV Pili and Cell Motility" Mol. Microbiol. 32(1):1-10 (1999).
U.S. Appl. No. 09/462,682, filed Apr. 28, 2000, Fitzgerald et al.
U.S. Appl. No. 10/110,880, filed Apr. 16, 2002, Fitzgerald et al.
U.S. Appl. No. 10/659,036, filed Sep. 9, 2003, Fitzgerald et al.
Ashorn, P. et al., "Elimination of infectious human immunodeficiency virus from human T-cell cultures by synergistic action of CD4-Pseudomonas exotoxin and reverse transcriptase inhibitors" PNAS USA 87:8889-8893 (1990).
Benhar, I. et al., "*Pseudomonas* Exotoxin A Mutants: Replacement of surface-exposed residues in domain III with cysteine residues that can be modified with polyethylene glycol in a site-specific manner" J. Biol. Chem. 269(18):13398-13404 (1994).
Berger, E. et al., "CD4-Pseudomonas exotoxin hybrid protein blocks the spread of human immunodeficiency virus infection in vitro and is active against cells expressing the envelope glycoproteins from diverse primate immunodeficiency retroviruses" PNAS USA 86:9539-9543 (1989).

(Continued)

*Primary Examiner*—Chih-Min Kam
(74) *Attorney, Agent, or Firm*—Townsend and Townsend and Crew LLP

(57) ABSTRACT

The invention provides chimeric proteins comprising a non-toxic *Pseudomonas* exotoxin A sequence and a Type IV pilin loop sequence, wherein the Type IV loop sequence is inserted within the non-toxic *Pseudomonas* exotoxin A. The invention also provides polynucleotides encoding the chimeric proteins, and compositions comprising the polynucleotides or the chimeric proteins. The invention also provides methods for using the chimeric proteins, polynucleotides and compositions of the invention.

13 Claims, 13 Drawing Sheets

OTHER PUBLICATIONS

Brinkmann, U. et al., "Alteration of a protease-sensitive region of *Pseudomonas* exotoxin prolongs its survival in the circulation of mice" PNAS USA 89:3065-3069 (1992).

Brinkmann, U. et al., "Independent domain folding of *Pseudomonas* exotoxin and single-chain immunotoxins: Influence of interdomain connections" PNAS USA 89:3075-3079 (1992).

Brinkmann, U. et al., "Immunotoxins against cancer" Biochimica et Biophysica Acta 1198:27-45 (1994).

Chaudhary, V. et al., "Selective killing of HIV-infected cells by recombinant human CD4-Pseudomonas exotoxin hybrid protein" Nature 335:369-372 (1988).

Chaudhary, V. et al., "*Pseudomonas* exotoxin contains a specific sequence at the carboxyl terminus that is required for cytotoxicity" PNAS USA 87:308-312 (1990).

Chaudhary, V. et al., "Mutagenesis of *Pseudomonas* exotoxin in identification of sequences responsible for the animal toxicity" J. Biol. Chem. 265(27):16303-16310 (1990).

Choe, M. et al., "B3(Fab)-PE38$^M$: A recombinant immunotoxin in which a mutant form of *Pseudomonas* exotoxin is fused to the Fab fragment of monoclonal antibody B3" Cancer Res. 54:3460-3467 (1994).

Cryz, Jr., S. et al., "Safety and immunogenicity of a *Pseudomonas aeruginosa* O-polysaccharide toxin A conjugate vaccine in humans" J. Clin. Invest. 80:51-56 (1987).

Cryz, Jr., S. et al., "Safety and immunogenicity of *Escherichia coli* O18 O-specific polysaccharide (O-PS)-toxin A and O-PS-cholera toxin conjugate vaccines in humans" J. Infect. Dis. 163:1040-1045 (1991).

Cryz, Jr., S. et al., "Human immunodeficiency virus-1 principal neutralizing domain peptide-toxin A conjugate vaccine" Vaccine 13(1):67-71 (1995).

Fattom, A. et al., "Comparative immunogenicity of conjugates composed of the *Staphylococcus aureus* type 8 capsular polysaccharide bound to carrier proteins by adipic acid dihydrazide or N-Succinimidyl-3-(2-pridyldithio)propionate" Infection and Immunity 60(2):584-589 (1992).

Fattom, A. et al., "Laboratory and clinical evaluation of conjugate vaccines composed of *Staphylococcus aureus* type 5 and type 8 capsular polysaccharides bound to *Pseudomonas aeruginosa* recombinant exoprotein A" Infection and Immunity 61(3):1023-1032 (1993).

Jinno, Y. et al., "Domain II mutants of *Pseudomonas* exotoxin deficient in translocation" J. Biol. Chem. 264(27):15953-15959 (1989).

Johnson, K. et al., "Nucleotide sequence and transcriptional initiation site of two *Pseudomonas aeruginosa* pilin genes" J. Biol. Chem. 261(33):15703-15708 (1986).

Kasturi, S. et al., "Alanine scanning mutagenesis identifies surface amino acids on domain III of *Pseudomonas* exotoxin required for cytotoxicity, proper folding, and secretion into periplasm" J. Biol. Chem. 267(32):23427-23433 (1992).

Kondo, T. et al., "Activity of immunotoxins constructed with modified *Pseudomona* exotoxin A lacking the cell recognition domain" J. Biol. Chem. 263(19):9470-9475 (1988).

Kreitman, R. et al., "Properties of chimeric toxins with two recognition domains: Interleukin 6 and transforming growth factor β at different locations in *Pseudomonas* exotoxin" Biocon. Chem 3:63-68 (1992).

Kuan, C. et al., "*Pseudomonas* exotoxin A mutants: Replacement of surface exposed residues in domain II with cysteine residues that can be modified with polyethylene glycol in a site-specific manner" J. Biol. Chem. 269(10):7610-7616 (1994).

Kuan, C. et al., "Improved antitumor activity of a recombinant anit-Lewis$^y$ immunotoxin not requiring proteolytic activation" PNAS USA 93:974-978 (1996).

Mansfield, E. et al., "Characterization of RFB4-Pseudomonas exotoxin A Immunotoxins targeted to CD22 on B-cell malignancies" Bioconj. Chem. 7:557-563 (1996).

Ogata, M. et al., "Processing of *Pseudomonas* exotoxin by a cellular protease results in the generation of a 37,000-da toxin fragment that is translocated to the cytosol" J. Biol. Chem> 265(33):20678-20685 (1990).

Ogata, M. et al., "Cell-mediated cleavage of *Pseudomonas* exotoxin between Arg$^{179}$ and Gly$^{280}$ generates the enzymatically active fragment which translocates to the cytosol" J. Biol. Chem. 267(35):25396-25401 (1992).

Pastan, I. et al., "*Pseudomonas* exotoxin: chimeric toxins" J. Biol. Chem. 264(26):15157-15160 (1989).

Que, J. et al., "Effect of carrier selection on immunogenicity of protein conjugate vaccines against Plasmodium falciparum circumsporozoites" Infect. and Immun. 56(10):2645-2649 (1988).

Reiter, Y. et al., "Engineering antibody Fv gragments for cancer detection and therapy: disulfide-stabilized Fv fragments" Nature Biotech. 14:1239-1245 (1996).

Seetharam, S. et al., "Increased cytotoxic activity of *Pseudomonas* exotoxin and two chimeric toxins ending in KDEL" J. Biol. Chem. 266(26):17376-17381 (1991).

Siegall, C. et al., "Functional analysis of domains II, Ib, and III of *Pseudomonas* exotoxin" J. Biol. Chem. 264(24):14256-14261 (1989).

Siegall, C. et al., "Analysis of sequences in domain II of *Pseudomonas* exotoxin A which mediate translocation" Biochemistry 30:7154-7159 (1991).

Theuer, C. et al., "A recombinant form of *Pseudomonas* exotoxin directed at the epidermal growth factor receptor that is cytotoxic without requiring proteolytic processing" J. Biol. Chem. 267(24):16872-16877 (1992).

Theuer, C. et al., "Immunotoxins made with a recombinant form of *Pseudomonas* exotoxin A that do not require proteolysis for activity" Cancer Res. 53:340-347 (1993).

Zdanovsky, A. et al., "Mechanism of action of *Pseudomonas* exotoxin" J. Biol. Chem. 268(29):21791-21799 (1993).

SEQUENCE LISTING

```
<160> NUMBER OF SEQ ID NOS: 36

<210> SEQ ID NO 1
<211> LENGTH: 1839
<212> TYPE: DNA
<213> ORGANISM: Pseudomonas aeruginosa
```

<220> FEATURE:
<221> NAME/KEY: CDS
<222> LOCATION: (1)..(1839)
<223> OTHER INFORMATION: mature form of Exotoxin A

<400> SEQUENCE: 1

| | | | | | | | | | | | | | | | | |
|---|---|---|---|---|---|---|---|---|---|---|---|---|---|---|---|---|
| gcc | gaa | gaa | gct | ttc | gac | ctc | tgg | aac | gaa | tgc | gcc | aaa | gcc | tgc | gtg | 48 |
| Ala | Glu | Glu | Ala | Phe | Asp | Leu | Trp | Asn | Glu | Cys | Ala | Lys | Ala | Cys | Val | |
| 1 | | | | 5 | | | | | 10 | | | | | 15 | | |
| ctc | gac | ctc | aag | gac | ggc | gtg | cgt | tcc | agc | cgc | atg | agc | gtc | gac | ccg | 96 |
| Leu | Asp | Leu | Lys | Asp | Gly | Val | Arg | Ser | Ser | Arg | Met | Ser | Val | Asp | Pro | |
| | | | 20 | | | | | 25 | | | | | 30 | | | |
| gcc | atc | gcc | gac | acc | aac | ggc | cag | ggc | gtg | ctg | cac | tac | tcc | atg | gtc | 144 |
| Ala | Ile | Ala | Asp | Thr | Asn | Gly | Gln | Gly | Val | Leu | His | Tyr | Ser | Met | Val | |
| | | | | 35 | | | | | 40 | | | | | 45 | | |
| ctg | gag | ggc | ggc | aac | gac | gcg | ctc | aag | ctg | gcc | atc | gac | aac | gcc | ctc | 192 |
| Leu | Glu | Gly | Gly | Asn | Asp | Ala | Leu | Lys | Leu | Ala | Ile | Asp | Asn | Ala | Leu | |
| | | 50 | | | | | 55 | | | | | 60 | | | | |
| agc | atc | acc | agc | gac | ggc | ctg | acc | atc | cgc | ctc | gaa | ggc | ggc | gtc | gag | 240 |
| Ser | Ile | Thr | Ser | Asp | Gly | Leu | Thr | Ile | Arg | Leu | Glu | Gly | Gly | Val | Glu | |
| 65 | | | | | 70 | | | | | 75 | | | | | 80 | |
| ccg | aac | aag | ccg | gtg | cgc | tac | agc | tac | acg | cgc | cag | gcg | cgc | ggc | agt | 288 |
| Pro | Asn | Lys | Pro | Val | Arg | Tyr | Ser | Tyr | Thr | Arg | Gln | Ala | Arg | Gly | Ser | |
| | | | | 85 | | | | | 90 | | | | | 95 | | |
| tgg | tcg | ctg | aac | tgg | ctg | gta | ccg | atc | ggc | cac | gag | aag | ccc | tcg | aac | 336 |
| Trp | Ser | Leu | Asn | Trp | Leu | Val | Pro | Ile | Gly | His | Glu | Lys | Pro | Ser | Asn | |
| | | | 100 | | | | | 105 | | | | | 110 | | | |
| atc | aag | gtg | ttc | atc | cac | gaa | ctg | aac | gcc | ggc | aac | cag | ctc | agc | cac | 384 |
| Ile | Lys | Val | Phe | Ile | His | Glu | Leu | Asn | Ala | Gly | Asn | Gln | Leu | Ser | His | |
| | | | | 115 | | | | | 120 | | | | | 125 | | |
| atg | tcg | ccg | atc | tac | acc | atc | gag | atg | ggc | gac | gag | ttg | ctg | gcg | aag | 432 |
| Met | Ser | Pro | Ile | Tyr | Thr | Ile | Glu | Met | Gly | Asp | Glu | Leu | Leu | Ala | Lys | |
| | | 130 | | | | | 135 | | | | | 140 | | | | |
| ctg | gcg | cgc | gat | gcc | acc | ttc | ttc | gtc | agg | gcg | cac | gag | agc | aac | gag | 480 |
| Leu | Ala | Arg | Asp | Ala | Thr | Phe | Phe | Val | Arg | Ala | His | Glu | Ser | Asn | Glu | |
| 145 | | | | | 150 | | | | | 155 | | | | | 160 | |
| atg | cag | ccg | acg | ctc | gcc | atc | agc | cat | gcc | ggg | gtc | agc | gtg | gtc | atg | 528 |
| Met | Gln | Pro | Thr | Leu | Ala | Ile | Ser | His | Ala | Gly | Val | Ser | Val | Val | Met | |
| | | | | 165 | | | | | 170 | | | | | 175 | | |
| gcc | cag | acc | cag | ccg | cgc | cgg | gaa | aag | cgc | tgg | agc | gaa | tgg | gcc | agc | 576 |
| Ala | Gln | Thr | Gln | Pro | Arg | Arg | Glu | Lys | Arg | Trp | Ser | Glu | Trp | Ala | Ser | |
| | | | 180 | | | | | 185 | | | | | 190 | | | |
| ggc | aag | gtg | ttg | tgc | ctg | ctc | gac | ccg | ctg | gac | ggg | gtc | tac | aac | tac | 624 |
| Gly | Lys | Val | Leu | Cys | Leu | Leu | Asp | Pro | Leu | Asp | Gly | Val | Tyr | Asn | Tyr | |
| | | | | 195 | | | | | 200 | | | | | 205 | | |
| ctc | gcc | cag | caa | cgc | tgc | aac | ctc | gac | gat | acc | tgg | gaa | ggc | aag | atc | 672 |
| Leu | Ala | Gln | Gln | Arg | Cys | Asn | Leu | Asp | Asp | Thr | Trp | Glu | Gly | Lys | Ile | |
| | | 210 | | | | | 215 | | | | | 220 | | | | |
| tac | cgg | gtg | ctc | gcc | ggc | aac | ccg | gcg | aag | cat | gac | ctg | gac | atc | aaa | 720 |
| Tyr | Arg | Val | Leu | Ala | Gly | Asn | Pro | Ala | Lys | His | Asp | Leu | Asp | Ile | Lys | |
| 225 | | | | | 230 | | | | | 235 | | | | | 240 | |
| ccc | acg | gtc | atc | agt | cat | cgc | ctg | cac | ttt | ccc | gag | ggc | ggc | agc | ctg | 768 |
| Pro | Thr | Val | Ile | Ser | His | Arg | Leu | His | Phe | Pro | Glu | Gly | Gly | Ser | Leu | |
| | | | | 245 | | | | | 250 | | | | | 255 | | |
| gcc | gcg | ctg | acc | gcg | cac | cag | gct | tgc | cac | ctg | ccg | ctg | gag | act | ttc | 816 |
| Ala | Ala | Leu | Thr | Ala | His | Gln | Ala | Cys | His | Leu | Pro | Leu | Glu | Thr | Phe | |
| | | | 260 | | | | | 265 | | | | | 270 | | | |
| acc | cgt | cat | cgc | cag | ccg | cgc | ggc | tgg | gaa | caa | ctg | gag | cag | tgc | ggc | 864 |
| Thr | Arg | His | Arg | Gln | Pro | Arg | Gly | Trp | Glu | Gln | Leu | Glu | Gln | Cys | Gly | |
| | | 275 | | | | | 280 | | | | | 285 | | | | |

-continued

| | | |
|---|---|---|
| tat ccg gtg cag cgg ctg gtc gcc ctc tac ctg gcg gcg cgg ctg tcg<br>Tyr Pro Val Gln Arg Leu Val Ala Leu Tyr Leu Ala Ala Arg Leu Ser<br>290                              295                          300 | 912 | |
| tgg aac cag gtc gac cag gtg atc cgc aac gcc ctg gcc agc ccc ggc<br>Trp Asn Gln Val Asp Gln Val Ile Arg Asn Ala Leu Ala Ser Pro Gly<br>305                              310                          315                       320 | 960 | |
| agc ggc ggc gac ctg ggc gaa gcg atc cgc gag cag ccg gag cag gcc<br>Ser Gly Gly Asp Leu Gly Glu Ala Ile Arg Glu Gln Pro Glu Gln Ala<br>                        325                          330                       335 | 1008 | |
| cgt ctg gcc ctg acc ctg gcc gcc gcc gag agc gag cgc ttc gtc cgg<br>Arg Leu Ala Leu Thr Leu Ala Ala Ala Glu Ser Glu Arg Phe Val Arg<br>                    340                          345                       350 | 1056 | |
| cag ggc acc ggc aac gac gag gcc ggc gcg gcc aac gcc gac gtg gtg<br>Gln Gly Thr Gly Asn Asp Glu Ala Gly Ala Ala Asn Ala Asp Val Val<br>355                              360                          365 | 1104 | |
| agc ctg acc tgc ccg gtc gcc gcc ggt gaa tgc gcg ggc ccg gcg gac<br>Ser Leu Thr Cys Pro Val Ala Ala Gly Glu Cys Ala Gly Pro Ala Asp<br>370                              375                          380 | 1152 | |
| agc ggc gac gcc ctg ctg gag cgc aac tat ccc act ggc gcg gag ttc<br>Ser Gly Asp Ala Leu Leu Glu Arg Asn Tyr Pro Thr Gly Ala Glu Phe<br>385                              390                          395                       400 | 1200 | |
| ctc ggc gac ggc ggc gac gtc agc ttc agc acc cgc ggc acg cag aac<br>Leu Gly Asp Gly Gly Asp Val Ser Phe Ser Thr Arg Gly Thr Gln Asn<br>                    405                          410                       415 | 1248 | |
| tgg acg gtg gag cgg ctg ctc cag gcg cac cgc caa ctg gag gag cgc<br>Trp Thr Val Glu Arg Leu Leu Gln Ala His Arg Gln Leu Glu Glu Arg<br>                    420                          425                       430 | 1296 | |
| ggc tat gtg ttc gtc ggc tac cac ggc acc ttc ctc gaa gcg gcg caa<br>Gly Tyr Val Phe Val Gly Tyr His Gly Thr Phe Leu Glu Ala Ala Gln<br>                        435                          440                       445 | 1344 | |
| agc atc gtc ttc ggc ggg gtg cgc gcg cgc agc cag gac ctc gac gcg<br>Ser Ile Val Phe Gly Gly Val Arg Ala Arg Ser Gln Asp Leu Asp Ala<br>450                              455                          460 | 1392 | |
| atc tgg cgc ggt ttc tat atc gcc ggc gat ccg gcg ctg gcc tac ggc<br>Ile Trp Arg Gly Phe Tyr Ile Ala Gly Asp Pro Ala Leu Ala Tyr Gly<br>465                              470                          475                       480 | 1440 | |
| tac gcc cag gac cag gaa ccc gac gca cgc ggc cgg atc cgc aac ggt<br>Tyr Ala Gln Asp Gln Glu Pro Asp Ala Arg Gly Arg Ile Arg Asn Gly<br>                    485                          490                       495 | 1488 | |
| gcc ctg ctg cgg gtc tat gtg ccg cgc tcg agc ctg ccg ggc ttc tac<br>Ala Leu Leu Arg Val Tyr Val Pro Arg Ser Ser Leu Pro Gly Phe Tyr<br>                    500                          505                       510 | 1536 | |
| cgc acc agc ctg acc ctg gcc gcg ccg gag gcg gcg ggc gag gtc gaa<br>Arg Thr Ser Leu Thr Leu Ala Ala Pro Glu Ala Ala Gly Glu Val Glu<br>                  515                         520                       525 | 1584 | |
| cgg ctg atc ggc cat ccg ctg ccg ctg cgc ctg gac gcc atc acc ggc<br>Arg Leu Ile Gly His Pro Leu Pro Leu Arg Leu Asp Ala Ile Thr Gly<br>530                              535                          540 | 1632 | |
| ccc gag gag gaa ggc ggg cgc ctg gag acc att ctc ggc tgg ccg ctg<br>Pro Glu Glu Glu Gly Gly Arg Leu Glu Thr Ile Leu Gly Trp Pro Leu<br>545                              550                          555                       560 | 1680 | |
| gcc gag cgc acc gtg gtg att ccc tcg gcg atc ccc acc gac ccg cgc<br>Ala Glu Arg Thr Val Val Ile Pro Ser Ala Ile Pro Thr Asp Pro Arg<br>                    565                          570                       575 | 1728 | |
| aac gtc ggc ggc gac ctc gac ccg tcc agc atc ccc gac aag gaa cag<br>Asn Val Gly Gly Asp Leu Asp Pro Ser Ser Ile Pro Asp Lys Glu Gln<br>                    580                          585                       590 | 1776 | |
| gcg atc agc gcc ctg ccg gac tac gcc agc cag ccc ggc aaa ccg ccg<br>Ala Ile Ser Ala Leu Pro Asp Tyr Ala Ser Gln Pro Gly Lys Pro Pro<br>595                              600                          605 | 1824 | |

```
cgc gag gac ctg aag                                                    1839
Arg Glu Asp Leu Lys
    610
```

<210> SEQ ID NO 2
<211> LENGTH: 613
<212> TYPE: PRT
<213> ORGANISM: Pseudomonas aeruginosa

<400> SEQUENCE: 2

```
Ala Glu Glu Ala Phe Asp Leu Trp Asn Glu Cys Ala Lys Ala Cys Val
1               5                   10                  15

Leu Asp Leu Lys Asp Gly Val Arg Ser Ser Arg Met Ser Val Asp Pro
            20                  25                  30

Ala Ile Ala Asp Thr Asn Gly Gln Gly Val Leu His Tyr Ser Met Val
        35                  40                  45

Leu Glu Gly Gly Asn Asp Ala Leu Lys Leu Ala Ile Asp Asn Ala Leu
    50                  55                  60

Ser Ile Thr Ser Asp Gly Leu Thr Ile Arg Leu Glu Gly Gly Val Glu
65                  70                  75                  80

Pro Asn Lys Pro Val Arg Tyr Ser Tyr Thr Arg Gln Ala Arg Gly Ser
                85                  90                  95

Trp Ser Leu Asn Trp Leu Val Pro Ile Gly His Glu Lys Pro Ser Asn
            100                 105                 110

Ile Lys Val Phe Ile His Glu Leu Asn Ala Gly Asn Gln Leu Ser His
        115                 120                 125

Met Ser Pro Ile Tyr Thr Ile Glu Met Gly Asp Glu Leu Leu Ala Lys
    130                 135                 140

Leu Ala Arg Asp Ala Thr Phe Phe Val Arg Ala His Glu Ser Asn Glu
145                 150                 155                 160

Met Gln Pro Thr Leu Ala Ile Ser His Ala Gly Val Ser Val Val Met
                165                 170                 175

Ala Gln Thr Gln Pro Arg Arg Glu Lys Arg Trp Ser Glu Trp Ala Ser
            180                 185                 190

Gly Lys Val Leu Cys Leu Leu Asp Pro Leu Asp Gly Val Tyr Asn Tyr
        195                 200                 205

Leu Ala Gln Gln Arg Cys Asn Leu Asp Asp Thr Trp Glu Gly Lys Ile
    210                 215                 220

Tyr Arg Val Leu Ala Gly Asn Pro Ala Lys His Asp Leu Asp Ile Lys
225                 230                 235                 240

Pro Thr Val Ile Ser His Arg Leu His Phe Pro Glu Gly Gly Ser Leu
                245                 250                 255

Ala Ala Leu Thr Ala His Gln Ala Cys His Leu Pro Leu Glu Thr Phe
            260                 265                 270

Thr Arg His Arg Gln Pro Arg Gly Trp Glu Gln Leu Glu Gln Cys Gly
        275                 280                 285

Tyr Pro Val Gln Arg Leu Val Ala Leu Tyr Leu Ala Ala Arg Leu Ser
    290                 295                 300

Trp Asn Gln Val Asp Gln Val Ile Arg Asn Ala Leu Ala Ser Pro Gly
305                 310                 315                 320

Ser Gly Gly Asp Leu Gly Glu Ala Ile Arg Glu Gln Pro Glu Gln Ala
                325                 330                 335

Arg Leu Ala Leu Thr Leu Ala Ala Glu Ser Glu Arg Phe Val Arg
            340                 345                 350
```

```
Gln Gly Thr Gly Asn Asp Glu Ala Gly Ala Asn Ala Asp Val Val
        355                 360                 365
Ser Leu Thr Cys Pro Val Ala Ala Gly Glu Cys Ala Gly Pro Ala Asp
    370                 375                 380
Ser Gly Asp Ala Leu Leu Glu Arg Asn Tyr Pro Thr Gly Ala Glu Phe
385                 390                 395                 400
Leu Gly Asp Gly Gly Asp Val Ser Phe Ser Thr Arg Gly Thr Gln Asn
                405                 410                 415
Trp Thr Val Glu Arg Leu Leu Gln Ala His Arg Gln Leu Glu Glu Arg
            420                 425                 430
Gly Tyr Val Phe Val Gly Tyr His Gly Thr Phe Leu Glu Ala Ala Gln
        435                 440                 445
Ser Ile Val Phe Gly Gly Val Arg Ala Arg Ser Gln Asp Leu Asp Ala
    450                 455                 460
Ile Trp Arg Gly Phe Tyr Ile Ala Gly Asp Pro Ala Leu Ala Tyr Gly
465                 470                 475                 480
Tyr Ala Gln Asp Gln Glu Pro Asp Ala Arg Gly Arg Ile Arg Asn Gly
                485                 490                 495
Ala Leu Leu Arg Val Tyr Val Pro Arg Ser Ser Leu Pro Gly Phe Tyr
            500                 505                 510
Arg Thr Ser Leu Thr Leu Ala Ala Pro Glu Ala Ala Gly Glu Val Glu
        515                 520                 525
Arg Leu Ile Gly His Pro Leu Pro Leu Arg Leu Asp Ala Ile Thr Gly
    530                 535                 540
Pro Glu Glu Glu Gly Gly Arg Leu Glu Thr Ile Leu Gly Trp Pro Leu
545                 550                 555                 560
Ala Glu Arg Thr Val Val Ile Pro Ser Ala Ile Pro Thr Asp Pro Arg
                565                 570                 575
Asn Val Gly Gly Asp Leu Asp Pro Ser Ser Ile Pro Asp Lys Glu Gln
            580                 585                 590
Ala Ile Ser Ala Leu Pro Asp Tyr Ala Ser Gln Pro Gly Lys Pro Pro
        595                 600                 605
Arg Glu Asp Leu Lys
    610

<210> SEQ ID NO 3
<211> LENGTH: 14
<212> TYPE: PRT
<213> ORGANISM: Artificial Sequence
<220> FEATURE:
<223> OTHER INFORMATION: Description of Artificial Sequence:Pseudomonas
      aeruginosa (PAK strain) Type IV short pilin loop

<400> SEQUENCE: 3

Cys Thr Ser Asp Gln Asp Glu Gln Phe Ile Pro Lys Gly Cys
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Description of Artificial Sequence:Pseudomonas
      aeruginosa (T2A strain) Type IV short pilin loop

<400> SEQUENCE: 4

Cys Thr Ser Thr Gln Asp Glu Met Phe Ile Pro Lys Gly Cys
1               5                   10
```

```
<210> SEQ ID NO 5
<211> LENGTH: 14
<212> TYPE: PRT
<213> ORGANISM: Artificial Sequence
<220> FEATURE:
<223> OTHER INFORMATION: Description of Artificial Sequence:Pseudomonas
      aeruginosa (PAO and 90063 strains) Type IV short
      pilin loop

<400> SEQUENCE: 5

Cys Lys Ser Thr Gln Asp Pro Met Phe Thr Pro Lys Gly Cys
1               5                   10

<210> SEQ ID NO 6
<211> LENGTH: 14
<212> TYPE: PRT
<213> ORGANISM: Artificial Sequence
<220> FEATURE:
<223> OTHER INFORMATION: Description of Artificial Sequence:Pseudomonas
      aeruginosa (CD and PA103 strains) Type IV short
      pilin loop

<400> SEQUENCE: 6

Cys Thr Ser Thr Gln Glu Glu Met Phe Ile Pro Lys Gly Cys
1               5                   10

<210> SEQ ID NO 7
<211> LENGTH: 14
<212> TYPE: PRT
<213> ORGANISM: Artificial Sequence
<220> FEATURE:
<223> OTHER INFORMATION: Description of Artificial Sequence:Pseudomonas
      aeruginosa (K122-4 strain) Type IV short pilin
      loop

<400> SEQUENCE: 7

Cys Thr Ser Asn Ala Asp Asn Lys Tyr Leu Pro Lys Thr Cys
1               5                   10

<210> SEQ ID NO 8
<211> LENGTH: 14
<212> TYPE: PRT
<213> ORGANISM: Artificial Sequence
<220> FEATURE:
<223> OTHER INFORMATION: Description of Artificial Sequence:Pseudomonas
      aeruginosa (KB7, 82932 and 82935 strains) Type IV
      short pilin loop

<400> SEQUENCE: 8

Cys Ala Thr Thr Val Asp Ala Lys Phe Arg Pro Asn Gly Cys
1               5                   10

<210> SEQ ID NO 9
<211> LENGTH: 14
<212> TYPE: PRT
<213> ORGANISM: Artificial Sequence
<220> FEATURE:
<223> OTHER INFORMATION: Description of Artificial Sequence:Pseudomonas
      aeruginosa (1071 strain) Type IV short pilin loop

<400> SEQUENCE: 9

Cys Glu Ser Thr Gln Asp Pro Met Phe Thr Pro Lys Gly Cys
1               5                   10

<210> SEQ ID NO 10
<211> LENGTH: 19
<212> TYPE: PRT
<213> ORGANISM: Artificial Sequence
```

```
<220> FEATURE:
<223> OTHER INFORMATION: Description of Artificial Sequence:Pseudomonas
      aeruginosa (577B strain) Type IV long pilin loop

<400> SEQUENCE: 10

Cys Asn Ile Thr Lys Thr Pro Thr Ala Trp Lys Pro Asn Tyr Ala Pro
1               5                   10                  15

Ala Asn Cys

<210> SEQ ID NO 11
<211> LENGTH: 19
<212> TYPE: PRT
<213> ORGANISM: Artificial Sequence
<220> FEATURE:
<223> OTHER INFORMATION: Description of Artificial Sequence:Pseudomonas
      aeruginosa (1244, 9D2 and P1 strains) Type IV long
      pilin loop

<400> SEQUENCE: 11

Cys Lys Ile Thr Lys Thr Pro Thr Ala Trp Lys Pro Asn Tyr Ala Pro
1               5                   10                  15

Ala Asn Cys

<210> SEQ ID NO 12
<211> LENGTH: 19
<212> TYPE: PRT
<213> ORGANISM: Artificial Sequence
<220> FEATURE:
<223> OTHER INFORMATION: Description of Artificial Sequence:Pseudomonas
      aeruginosa (SBI-N strain) Type IV long pilin loop

<400> SEQUENCE: 12

Cys Gly Ile Thr Gly Ser Pro Thr Asn Trp Lys Ala Asn Tyr Ala Pro
1               5                   10                  15

Ala Asn Cys

<210> SEQ ID NO 13
<211> LENGTH: 33
<212> TYPE: PRT
<213> ORGANISM: Artificial Sequence
<220> FEATURE:
<223> OTHER INFORMATION: Description of Artificial Sequence:Neisseria
      meningitidis (Z49820 strain) Type IV pilin loop

<400> SEQUENCE: 13

Cys Gly Leu Pro Val Ala Arg Asp Asp Thr Asp Ser Ala Thr Asp Val
1               5                   10                  15

Lys Ala Asp Thr Thr Asp Asn Ile Asn Thr Lys His Leu Pro Ser Thr
            20                  25                  30

Cys

<210> SEQ ID NO 14
<211> LENGTH: 37
<212> TYPE: PRT
<213> ORGANISM: Artificial Sequence
<220> FEATURE:
<223> OTHER INFORMATION: Description of Artificial Sequence:Neisseria
      meningitidis (Z69262 strain) Type IV pilin loop

<400> SEQUENCE: 14

Cys Gly Gln Pro Val Thr Arg Gly Ala Gly Asn Ala Gly Lys Ala Asp
1               5                   10                  15

Asp Val Thr Lys Ala Gly Asn Asp Asn Glu Lys Ile Asn Thr Lys His
            20                  25                  30
```

-continued

```
Leu Pro Ser Thr Cys
        35

<210> SEQ ID NO 15
<211> LENGTH: 31
<212> TYPE: PRT
<213> ORGANISM: Artificial Sequence
<220> FEATURE:
<223> OTHER INFORMATION: Description of Artificial Sequence:Neisseria
      meningitidis (Z69261 strain) Type IV pilin loop

<400> SEQUENCE: 15

Cys Gly Gln Pro Val Thr Arg Ala Lys Ala Asp Ala Asp Ala Ala Gly
1               5                   10                  15

Lys Asp Thr Thr Asn Ile Asp Thr Lys His Leu Pro Ser Thr Cys
            20                  25                  30

<210> SEQ ID NO 16
<211> LENGTH: 33
<212> TYPE: PRT
<213> ORGANISM: Artificial Sequence
<220> FEATURE:
<223> OTHER INFORMATION: Description of Artificial Sequence:Neisseria
      gonorrhoeae (pilE; X66144 strain) Type IV pilin
      loop

<400> SEQUENCE: 16

Cys Gly Gln Pro Val Thr Arg Thr Gly Asp Asn Asp Asp Thr Val Ala
1               5                   10                  15

Asp Ala Lys Asp Gly Lys Glu Ile Asp Thr Lys His Leu Pro Ser Thr
            20                  25                  30

Cys

<210> SEQ ID NO 17
<211> LENGTH: 35
<212> TYPE: PRT
<213> ORGANISM: Artificial Sequence
<220> FEATURE:
<223> OTHER INFORMATION: Description of Artificial Sequence:Neisseria
      gonorrhoeae (pilE; AF043648 strain) Type IV pilin
      loop

<400> SEQUENCE: 17

Cys Gly Gln Pro Val Lys Arg Asp Ala Gly Ala Lys Thr Gly Ala Asp
1               5                   10                  15

Asp Val Lys Ala Asp Gly Asn Asn Gly Ile Asn Thr Lys His Leu Pro
            20                  25                  30

Ser Thr Cys
        35

<210> SEQ ID NO 18
<211> LENGTH: 67
<212> TYPE: PRT
<213> ORGANISM: Artificial Sequence
<220> FEATURE:
<223> OTHER INFORMATION: Description of Artificial Sequence:Vibrio
      cholera (U09807 strain) Type IV pilin loop

<400> SEQUENCE: 18

Cys Lys Thr Leu Val Thr Ser Val Gly Asp Met Phe Pro Phe Ile Asn
1               5                   10                  15

Val Lys Glu Gly Ala Phe Ala Ala Val Ala Asp Leu Gly Asp Phe Glu
            20                  25                  30
```

-continued

```
Thr Ser Val Ala Asp Ala Ala Thr Gly Ala Gly Val Ile Lys Ser Ile
        35                  40                  45

Ala Pro Gly Ser Ala Asn Leu Asn Leu Thr Asn Ile Thr His Val Glu
    50                  55                  60

Lys Leu Cys
65

<210> SEQ ID NO 19
<211> LENGTH: 67
<212> TYPE: PRT
<213> ORGANISM: Artificial Sequence
<220> FEATURE:
<223> OTHER INFORMATION: Description of Artificial Sequence:Vibrio
      cholera (X64098 strain) Type IV pilin loop

<400> SEQUENCE: 19

Cys Lys Thr Leu Ile Thr Ser Val Gly Asp Met Phe Pro Tyr Ile Ala
1               5                   10                  15

Ile Lys Ala Gly Gly Ala Val Ala Leu Ala Asp Leu Gly Asp Phe Glu
            20                  25                  30

Asn Ser Ala Ala Ala Ala Glu Thr Gly Val Gly Val Ile Lys Ser Ile
        35                  40                  45

Ala Pro Ala Ser Lys Asn Leu Asp Leu Thr Asn Ile Thr His Val Glu
    50                  55                  60

Lys Leu Cys
65

<210> SEQ ID NO 20
<211> LENGTH: 13
<212> TYPE: PRT
<213> ORGANISM: Artificial Sequence
<220> FEATURE:
<223> OTHER INFORMATION: Description of Artificial Sequence:Pasteurella
      multocida (AF154834 strain) Type IV pilin loop

<400> SEQUENCE: 20

Cys Asn Gly Gly Ser Glu Val Phe Pro Ala Gly Phe Cys
1               5                   10

<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence:endoplasmic
      reticulum (ER) retention domain in native
      Pseudomonas exotoxin A

<400> SEQUENCE: 21

Arg Glu Asp Leu Lys
1               5

<210> SEQ ID NO 22
<211> LENGTH: 4
<212> TYPE: PRT
<213> ORGANISM: Artificial Sequence
<220> FEATURE:
<223> OTHER INFORMATION: Description of Artificial Sequence:endoplasmic
      reticulum (ER) retention domain

<400> SEQUENCE: 22

Arg Glu Asp Leu
1
```

```
<210> SEQ ID NO 23
<211> LENGTH: 4
<212> TYPE: PRT
<213> ORGANISM: Artificial Sequence
<220> FEATURE:
<223> OTHER INFORMATION: Description of Artificial Sequence:endoplasmic
      reticulum (ER) retention domain

<400> SEQUENCE: 23

Arg Glu Asp Leu
1

<210> SEQ ID NO 24
<211> LENGTH: 25
<212> TYPE: DNA
<213> ORGANISM: Artificial Sequence
<220> FEATURE:
<223> OTHER INFORMATION: Description of Artificial Sequence:Forward
      primer

<400> SEQUENCE: 24
ggcccatatg cacctgatac cccat                                      25

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence:Reverse
      primer

<400> SEQUENCE: 25
gaattcagtt acttcaggtc ctcg                                       24

<210> SEQ ID NO 26
<211> LENGTH: 28
<212> TYPE: DNA
<213> ORGANISM: Artificial Sequence
<220> FEATURE:
<223> OTHER INFORMATION: Description of Artificial Sequence:Forward
      primer

<400> SEQUENCE: 26
ggcccatatg gagggcggca gcctggcc                                   28

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence:Reverse
      primer

<400> SEQUENCE: 27
gaattcagtt acttcaggtc ctcg                                       24

<210> SEQ ID NO 28
<211> LENGTH: 26
<212> TYPE: DNA
<213> ORGANISM: Artificial Sequence
<220> FEATURE:
<223> OTHER INFORMATION: Description of Artificial Sequence:PCR primer
      pilATG (26 nc)

<400> SEQUENCE: 28
gagatattca tgaaagctca aaaagg                                     26
```

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence:PCR primer
      nadB4 (20 nc)

<400> SEQUENCE: 29
atctccatcg gcaccctgac                                                 20

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence:PCR primer
      nadB1 (21 nc)

<400> SEQUENCE: 30
tggaagtgga agtggagaac c                                               21

<210> SEQ ID NO 31
<211> LENGTH: 90
<212> TYPE: DNA
<213> ORGANISM: Artificial Sequence
<220> FEATURE:
<223> OTHER INFORMATION: Description of Artificial Sequence:coding
      strand of duplex

<400> SEQUENCE: 31
tggccctgac cctggccgcc gccgagagcg agcgcttcgt ccggcagggc accggcaacg     60
acgaggccgg cgcggcaaac ctgcagggcc                                      90

<210> SEQ ID NO 32
<211> LENGTH: 54
<212> TYPE: DNA
<213> ORGANISM: Artificial Sequence
<220> FEATURE:
<223> OTHER INFORMATION: Description of Artificial Sequence:Sense
      oligonucleotide

<400> SEQUENCE: 32
ttgtactagt gatcaggatg aacagtttat tccgaaaggt tgttcacgta tgca           54

<210> SEQ ID NO 33
<211> LENGTH: 54
<212> TYPE: DNA
<213> ORGANISM: Artificial Sequence
<220> FEATURE:
<223> OTHER INFORMATION: Description of Artificial Sequence:Antisense
      oligonucleotide

<400> SEQUENCE: 33
tacgtgaaca acctttcgga ataaactgtt catcctgatc actagtacaa tgca           54

<210> SEQ ID NO 34
<211> LENGTH: 17
<212> TYPE: PRT
<213> ORGANISM: Artificial Sequence
<220> FEATURE:
<223> OTHER INFORMATION: Description of Artificial Sequence:long
      C-terminal peptide, peptide 1, amino acids 128-142 of PAK
      strain
<220> FEATURE:
<221> NAME/KEY: MOD_RES
<222> LOCATION: (1)
<223> OTHER INFORMATION: Xaa = acetyl-lysine

```
-continued

<220> FEATURE:
<221> NAME/KEY: MOD_RES
<222> LOCATION: (17)
<223> OTHER INFORMATION: Xaa = lysinamide

<400> SEQUENCE: 34

Xaa Cys Thr Ser Asp Gln Asp Glu Gln Phe Ile Pro Lys Gly Cys Ser
1               5                   10                  15

Xaa

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence:core
      peptide, peptide 2, amino acids 134-140 of PAK strain
<220> FEATURE:
<221> NAME/KEY: MOD_RES
<222> LOCATION: (1)
<223> OTHER INFORMATION: Xaa = acetyl-aspartic acid
<220> FEATURE:
<221> NAME/KEY: MOD_RES
<222> LOCATION: (7)
<223> OTHER INFORMATION: Xaa = lysinamide

<400> SEQUENCE: 35

Xaa Glu Gln Phe Ile Pro Xaa
1               5

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence:scrambled
      peptide
<220> FEATURE:
<221> NAME/KEY: MOD_RES
<222> LOCATION: (1)
<223> OTHER INFORMATION: Xaa = acetyl-glutamine
<220> FEATURE:
<221> NAME/KEY: MOD_RES
<222> LOCATION: (7)
<223> OTHER INFORMATION: Xaa = lysinamide

<400> SEQUENCE: 36

Xaa Ile Asp Pro Glu Phe Xaa
1               5
```

CHIMERIC PROTEIN COMPRISING NON-TOXIC *PSEUDOMONAS* EXOTOXIN A AND TYPE IV PILIN SEQUENCES

CROSS-REFERENCES TO RELATED APPLICATIONS

This application is a 371 of PCT/US01/49143, filed Dec. 20, 2001, which claims priority of U.S. Provisional Application No. 60/257,877, filed Dec. 21, 2000, the contents of which is incorporated herein by reference in their entirety.

STATEMENT AS TO RIGHTS TO INVENTIONS MADE UNDER FEDERALLY SPONSORED RESEARCH AND DEVELOPMENT

Not Applicable.

BACKGROUND OF THE INVENTION

Type IV pilin is the major subunit of the pilus or pili which are filamentous structures covering many microorganisms including bacteria and yeast. Among these microorganisms, many pathogenic species express Type IV pilins, including, e.g., *P. aeruginosa, N. meningitides, N. gonorrhoeae, Vibro cholera,* and *Pasteurella multocidam.* The first step in infection with these pathogenic microorganisms is adherence to target cells through the pili. In particular, Type IV pilins of *Pseudomonas aeruginosa* bind to asialoGM1 receptors on epithelial cells (Saiman et al., *J. Clin. Invest.* 92(4):1875–80 (1993); Sheth et al., 11(4):715–23 (1994); Imundo et al., *Proc. Natl. Acad. Sci. USA,* 92(7):3019–23 (1995); Hahn, *Gene* 192(1):99–108 (1997)). Thus, the pili of these microorganisms are a major virulence factor, and result in colonization by pathogenic microorganisms and infections in humans.

For example, *Pseudomonas aeruginosa* causes between 10% and 20% infections in most hospitals. *Pseudomonas* infection is common among patients with cystic fibrosis, burn wounds, organ transplants, and intravenous-drug addiction. *Pseudomonas* infections can lead to serious conditions, such as endophthalmitis, endocarditis, meningitis, pneumonia, and septicemia. In particular, colonization of cystic fibrosis (CF) individuals with *Pseudomonas aeruginosa* represents a significant negative milestone in the progression of this disease. Once colonized, patients are subject to the damaging effects of various secreted virulence factors and to the inflammatory response of the host immune system.

Type IV pili are composed of pilin polymers arranged in a helical structure with five subunits per turn (Forest et al., *Gene* 192(1): 165–9 (1997); Parge, *Nature* 378(6552):32–8 (1995)). The portion of the pilin protein responsible for cell binding is found near the C-terminus (amino acids 122–148) in a β-turn loop subtended from a disulfide bond (Campbell et al., *Biochemistry* 36(42):12791–801 (1997); Campbell et al., *J. Mol. Biol.* 267(2):382–402 (1997); Hazes et al., *J. Mol. Biol.* 299(4):1005–1017 (2000); McInnes et al., *Biochemistry* 32(49):13432–40 (1993)). For *P. aeruginosa,* a 12 or 17 amino acid sequence (depending on the strain) in this loop interacts with receptors on epithelial cells. For CF individuals, the overproduction of the R domain of mutant cystic fibrosis transmembrane conductance regulator (CFTR) can lead to an increased level of asialoGM1 and, accordingly, an increased binding of *P. aeruginosa* (Imundo et al., *Proc. Natl. Acad. Sci. USA* 92(7):3019–23 (1995); Saiman et al., *J. Clin. Invest.* 92(4):1875–80 (1993); Bryan et al., *Am. J. Respir. Cell Mol. Biol.* 19(2):269–77 (1998); Imundo et al., *Proc. Natl. Acad. Sci. USA* 92(7):3019–23 (1995); Saiman et al., *J. Clin. Invest.* 92(4):1875–80 (1993)). Functional studies of pilin have indicated that only the last pilin subunit (the tip) of a pilus interacts with epithelial cell receptors (Lee et al., *Mol. Microbiol.* 11(4):705–13 (1994)).

To date, efforts to produce an effective anti-pilin vaccine have not been very successful. In part, this limited success is because the most immunogenic portion of the protein (the middle) does not generate antibodies that interfere with adhesion. Unfortunately, the C-terminal loop of pilin is not very immunogenic, and high titer responses have only been reported with the use of strategies that employ multiple display copies of the loop sequence (Hahn et al., *Behring. Inst. Mitt.* (98):315–25 (1997)). For CF patients, strategies to inhibit *Pseudomonas* colonization are considered an important element in reducing the morbidity normally associated with the development of chronic infections (Tang et al., *Infect. Immun.* 63(4):1278–85 (1995); Li et al., *Proc. Natl. Acad. Sci. USA* 94(3):967–72 (1997); Tang et al., *Infect. Immun.* 63(4):1278–85 (1995) Doig, P. et al., *Infect Immun* 58(1):124–30 (1990); El-Zaim, H. S. et al. *Infect Immun* 66(11):5551–4 (1998)).

Accordingly, there is a need to develop compositions for reducing or preventing infections by pathogenic microorganisms including, in particular, *Pseudomonas aeruginosa.* Embodiments of this invention address this and other needs.

SUMMARY OF THE INVENTION

Embodiments of the invention provide chimeric proteins comprising a non-toxic *Pseudomonas* exotoxin A sequence and a Type IV pilin loop sequence, wherein the Type IV pilin loop sequence is located within the non-toxic *Pseudomonas* exotoxin A sequence. In the present invention, a Type IV pilin loop sequence refers to the sequence that forms an intrachain disulfide loop at the C-terminus of the pilin. This loop interacts and binds to receptors on epithelial cells. The present invention is based on, in part, the discovery that the Type IV pilin loop sequence within the *Pseudomonas* exotoxin A sequence is presented in near-native conformation, and can react with receptors on epithelial cells. As a result, the present chimeric protein comprises the Type IV pilin loop sequence which competes for binding to these epithelial cells, and which can reduce adherence of pathogenic microorganisms expressing the Type IV pilin to the epithelial cells. Therefore, the chimeric protein can be used on its own or in a composition to directly reduce adherence of pathogenic microorganisms in a host.

The present invention is also based on, in part, the discovery that antisera generated against the chimeric proteins of the invention are also useful in reducing adherence of pathogenic microorganisms (expressing Type IV pilins) in a host. Since the chimeric protein presents the Type IV pilin loop in near-native conformation, the chimeric proteins of the invention, when introduced into a host, generate polyclonal antisera that bind to the pilin loop portion of the chimeric proteins. The antisera can also bind to Type IV pilins on pathogenic microorganism, and thus competitively inhibit binding of the pathogenic microorganisms to epithelial cell receptors. Accordingly, the chimeric protein can be used as a vaccine to generate antisera in a host which can result in reduction of both adherence and colonization of pathogenic microorganisms in the host.

Furthermore, since the chimeric protein presents the non-toxic *Pseudomonas* exotoxin A sequence in near-native conformation, the chimeric proteins of the invention, when introduced into a host, generate polyclonal antisera that bind to the non-toxic *Pseudomonas* exotoxin A as well as to the native *Pseudomonas* exotoxin A. The native *Pseudomonas* exotoxin A which is secreted by *Pseudomonas aeruginosa* is known to cause cell cytotoxicity by entering into cells by receptor-mediated endocytosis and then, after a series of intracellular processing steps, translocate to the cell cytosol and ADP-ribosylate elongation factor 2. This results in the inhibition of protein synthesis and cell death. The antisera generated against the present chimeric protein can bind exotoxin A released from *Pseudomonas* and can neutralize cell cytotoxicity. Therefore, should small numbers of *Pseudomonas* overcome the first line of defense (antibodies against the pilin loop sequence preventing colonization), the normal destructive power of the exotoxin A will be neutralized by antibodies generated against the non-toxic *Pseudomonas* exotoxin A sequence.

The chimeric proteins, the chimeric polynucleotides, and the compositions of the present invention have many other utilities. For example, the chimeric proteins and the compositions comprising chimeric proteins can be used to in diagnostic tests, such as immunoassays. Such diagnostic tests can be used to detect the presence of microorganisms bearing a Type IV pilin loop sequence, such as *Pseudomonas aeruginosa*, or to determine whether a host has antisera against a Type IV pilin loop due to an infection. In another example, the chimeric proteins and the compositions comprising the chimeric proteins can also be used to purify antibodies against, e.g., the Type IV pilin loop sequence. In another example, the antibodies against the chimeric protein can be used to clone and isolate other related Type IV pilin sequences.

Accordingly, in one aspect of the invention, the invention provides a chimeric protein comprising: a non-toxic *Pseudomonas* exotoxin A sequence and a Type IV pilin loop sequence, the Type IV pilin loop sequence being located within the non-toxic *Pseudomonas* exotoxin A sequence, wherein the chimeric protein is capable of reducing adherence of a microorganism expressing the Type IV pilin loop sequence to epithelial cells, and further wherein the chimeric protein, when introduced into a host, is capable of generating polyclonal antisera that reduce adherence of the microorganism expressing the Type IV pilin loop sequence to the epithelial cells.

In another aspect, the invention provides a chimeric protein comprising: (a) a non-toxic *Pseudomonas* exotoxin A sequence comprising domain Ia, domain II, and domain III; and (b) a Type IV pilin loop sequence, wherein the Type IV pilin loop sequence is located between domain II and domain III of the non-toxic *Pseudomonas* exotoxin A sequence.

In another aspect, the invention provides a polynucleotide encoding a chimeric protein, the chimeric protein comprising: a non-toxic *Pseudomonas* exotoxin A sequence and a Type IV pilin loop sequence, the Type IV pilin loop sequence being located within the non-toxic *Pseudomonas* exotoxin A sequence, wherein the chimeric protein is capable of reducing adherence of a microorganism expressing the Type IV pilin loop sequence to epithelial cells, and further wherein the chimeric protein, when introduced into a host, is capable of generating polyclonal antisera that prevent adherence of the microorganism expressing the Type IV pilin loop sequence to the epithelial cells.

In another aspect, the invention provides a polynucleotide encoding a chimeric protein, the chimeric protein comprising: (a) a non-toxic *Pseudomonas* exotoxin A sequence comprising domain Ia, domain II, and domain III; and (b) a Type IV pilin loop sequence, wherein the Type IV pilin loop sequence is located between domain II and domain III of the non-toxic *Pseudomonas* exotoxin A sequence.

In another aspect, the invention provides a composition comprising a chimeric protein, the chimeric protein comprising: a non-toxic *Pseudomonas* exotoxin A sequence and a Type IV pilin loop sequence, the Type IV pilin loop sequence being located within the non-toxic *Pseudomonas* exotoxin A sequence, wherein the chimeric protein is capable of reducing adherence of a microorganism expressing the Type IV pilin loop sequence to epithelial cells, and further wherein the chimeric protein, when introduced into a host, is capable of generating polyclonal antisera that prevent adherence of the microorganism expressing the Type IV pilin loop sequence to the epithelial cells.

In another aspect, the invention provides a method for eliciting an immune response in a host, the method comprising the step of administering to the host an immunologically effective amount of a composition comprising a chimeric protein comprising: a non-toxic *Pseudomonas* exotoxin A sequence and a Type IV pilin loop sequence, the Type IV pilin loop sequence being located within the non-toxic *Pseudomonas* exotoxin A sequence, wherein the chimeric protein is capable of reducing adherence of a microorganism expressing the Type IV pilin loop sequence to epithelial cells, and further wherein the chimeric protein, when introduced into the host, is capable of generating polyclonal antisera that prevent adherence of the microorganism expressing the Type IV pilin loop sequence to the epithelial cells.

In another aspect, the invention provides a method of eliciting an immune response in a host, the method comprising the step of administering to the host an immunologically effective amount of an expression cassette comprising a polynucleotide encoding a chimeric protein comprising: a non-toxic *Pseudomonas* exotoxin A sequence and a Type IV pilin loop sequence, the Type IV pilin loop sequence being located within the non-toxic *Pseudomonas* exotoxin A, wherein the chimeric protein is capable of reducing adherence of a microorganism expressing the Type IV pilin loop sequence to epithelial cells, and further wherein the chimeric protein, when introduced into the host, is capable of generating polyclonal antisera that reduce adherence of the microorganism expressing the Type IV pilin loop sequence to the epithelial cells.

In another aspect, the invention provides a method of generating antibodies specific for a Type IV pilin loop sequence, comprising introducing into a host a composition comprising a chimeric protein comprising a non-toxic *Pseudomonas* exotoxin A sequence and a Type IV pilin loop sequence, the Type IV pilin loop sequence being located within the non-toxic *Pseudomonas* exotoxin A, wherein the chimeric protein is capable of reducing adherence of a microorganism expressing the Type IV pilin loop sequence to epithelial cells, and further wherein the chimeric protein, when introduced into the host, is capable of generating polyclonal antisera that reduce adherence of the microorganism expressing the Type IV pilin loop sequence to epithelial cells.

DEFINITIONS

Figure 1A:
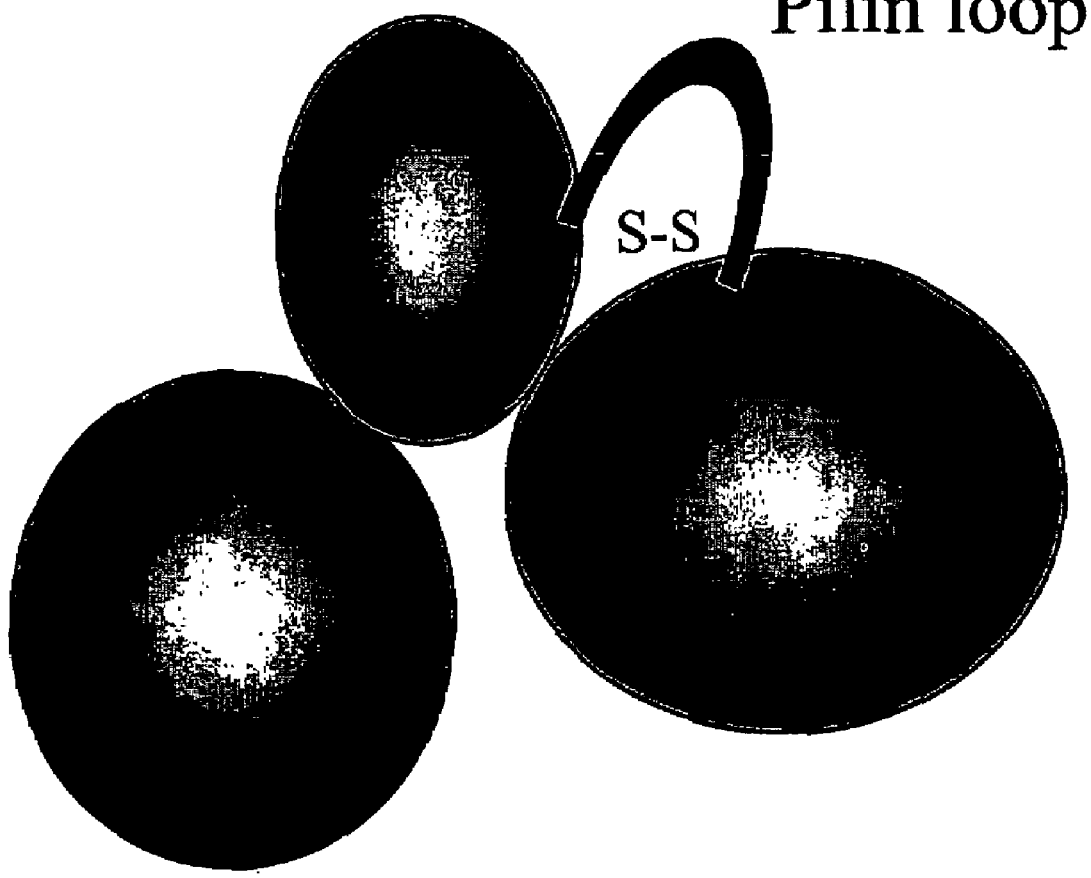
FIG. 1A illustrates in cartoon form the replacement of domain Ib with the C-terminal loop of pilin. The pilin insert corresponds to the sequence of pilin reported for the PAK strain of *P. aeruginosa*.
Figure 1B:
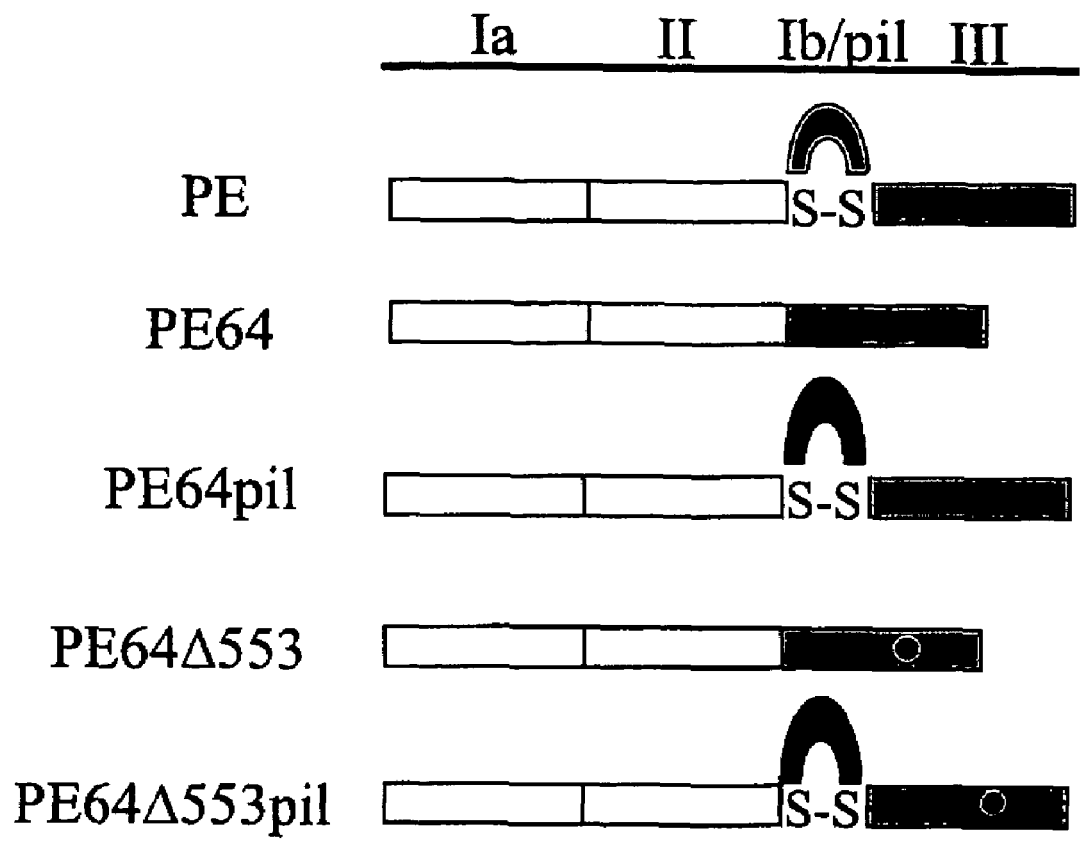
FIG. 1B illustrates in cartoon form the domain structure of PE from Allured et al., *Proc. Natl. Acad. Sci.* 83:1320–1324 (1986). PE64 lacks the loop region of domain Ib. PE64pil includes the insertion of the pilin loop (residues 129–142) of the PAK strain of *P. aeruginosa*. The deletion of glutamic acid 553 (indicated by a dot) removes an active site residue (Lukac et al., *Infect. Immuno.* 56(12):3095–8 (1988)) and produces proteins PE64Δ553 and PE64Δ553pil with no ADP-ribosylating activity. The Ib loop is shown in light shading and the pilin loop in darker shading.
Figure 2:
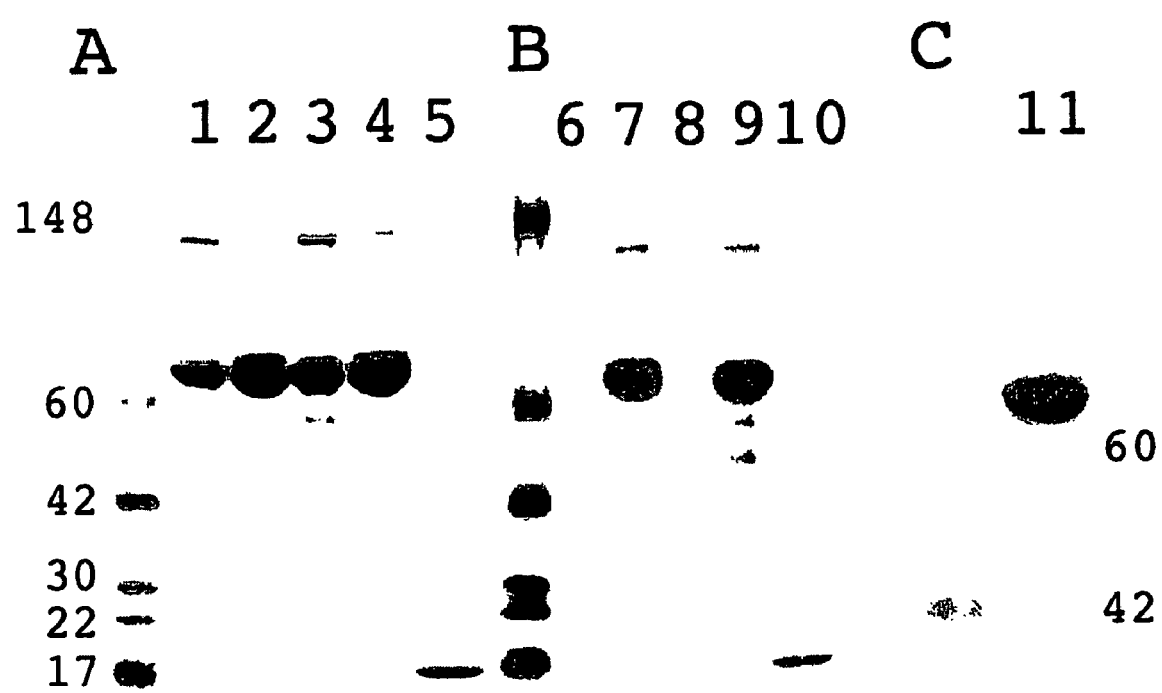
FIG. 2 illustrates SDS PAGE (Panel A and C) and Western blot analysis (Panel B) of PE proteins and pilin. A. Lanes 1–4 show substantially pure PE proteins (4–5 μg of protein was loaded per lane) after MonoQ chromatography. From left to right the proteins loaded were: PE64, PE64pil, PE64Δ553 and PE64Δ553pil. Purified PAK pilin was added to lane 5. B. Lanes 6–10 show the same proteins as A but probed with a monoclonal antibody to the pilin loop. Lane 11 is PE64Δ553pil after gel filtration chromatography. Standard proteins and their molecular masses in kDa are indicated.

"*Pseudomonas* exotoxin A" or "PE" is secreted by *P. aeruginosa* as a 67 kDa protein composed of three prominent globular domains (Ia, II, and III) and one small subdomain (Ib) connecting domains II and III. (Allured et. al., *Proc. Natl. Acad. Sci.* 83:1320–1324 (1986).) Domain Ia of PE located at the N-terminus and mediates cell binding. In nature, domain Ia binds to the low density lipoprotein receptor-related protein ("LRP"), also known as the α2-macroglobulin receptor ("α2-MR"). (Kounnas et al., *J. Biol. Chem.* 267:12420–23 (1992).) It spans amino acids 1–252. Domain II mediates translocation to the cytosol. It spans amino acids 253–364. Domain Ib has no known function. It spans amino acids 365–399. Domain III is responsible for cytotoxicity and includes an endoplasmic reticulum retention sequence. It mediates ADP ribosylation of elongation factor 2 ("EF2"), which inactivates protein synthesis. It spans amino acids 400–613. The native *Pseudomonas aeruginosa* exotoxin A nucleic acid sequence and the amino acid sequence are shown as SEQ ID NO:1 and SEQ ID NO:2, respectively. SEQ ID NOS: 1 and 2 are the mature form of exotoxin A, wherein the signal sequence has been cleaved off. As a virulence factor, PE can kill PMNs, macrophages and other elements of the immune system (Pollack et al., *Infect. Immuno.* 19(3):1092–6 (1978)).

As used herein, "*Pseudomonas* exotoxin A" or "PE" refer to those having the functions described above and includes the native *Pseudomonas* exotoxin A having the nucleic acid and amino acid sequences (as shown as SEQ ID NO:1 and SEQ ID NO:2, respectively) and also polymorphic variants, alleles, mutants and interspecies homologs that: (1) have about 80% amino acid sequence identity, preferably about 85–90% amino acid sequence identity to SEQ ID NO:2 over a window of about 25 amino acids, preferably over a window of about 50–100 amino acids; (2) bind to antibodies raised against an immunogen comprising an amino acid sequence of SEQ ID NO:2 and conservatively modified variants thereof; or (3) specifically hybridize (with a size of at least about 500, preferably at least about 900 nucleotides) under stringent hybridization conditions to a sequence SEQ ID NO:1 and conservatively modified variants thereof. For example, genetically modified forms of PE are described in, e.g., Pastan et al., U.S. Pat. No. 5,602,095; Pastan et al., U.S. Pat. No. 5,512,658 and Pastan et al., U.S. Pat. No. 5,458,878. Allelic forms of PE are included in this definition. See, e.g., Vasil et al., *Infect. Immunol.* 52:538–48 (1986).

"Non-toxic *Pseudomonas* exotoxin A" or "non-toxic PE" refers to any *Pseudomonas* exotoxin A described herein (including modified variants) that lacks ADP ribosylation activity. The ribosylating activity of PE is located between about amino acids 400 and 600 of PE. For example, deleting amino acid E553 ("ΔE553") from domain III detoxifies the molecule. This detoxified PE is referred to as "PE ΔE553." In another example, substitution of histidine residue of PE at 426 with a tyrosine residue also inactivates the ADP-ribosylation of PE (see Kessler & Galloway, *J. Biol. Chem.* 267:19107–11 (1992)). Other amino acids within domain III can be modified by, e.g., deletion, substitution or addition of amino acid residues, to eliminate ADP ribosylation activity. Domain III of non-toxic PE is sometimes referred to herein as "detoxified domain III."

The term "a non-toxic *Pseudomonas* exotoxin A sequence" is used generically to refer to either a nucleic acid sequence or an amino acid sequence of non-toxic *Pseudomonas* exotoxin A. As used herein, a non-toxic *Pseudomonas* exotoxin A sequence may be a full length sequence or portion(s) of the full length sequence. Generally, a non-toxic *Pseudomonas* exotoxin A sequence has one or more domains or portions of domains with certain biological activities of a non-toxic *Pseudomonas* exotoxin A, such as a cell recognition domain, a translocation domain, or an endoplasmic reticulum retention domain. For example, a non-toxic *Pseudomonas* exotoxin A sequence may include only domain II and detoxified domain III. In another example, a non-toxic *Pseudomonas* exotoxin A sequence may include only domain Ia, domain II, and detoxified domain III. In another example, a non-toxic *Pseudomonas* exotoxin A sequence may include all of domains Ia, Ib, II, and detoxified III. Therefore, a non-toxic *Pseudomonas* exotoxin A sequence may be a contiguous sequence of the native *Pseudomonas* exotoxin A, or it can be a sequence comprised of non-contiguous subsequences of the native *Pseudomonas* exotoxin A that lacks ADP ribosylation activity. While a non-toxic *Pseudomonas* exotoxin A sequence may be smaller contiguous or non-contiguous portion(s) of the native PE, the numberings of the native PE amino acid and nucleic acid sequences are used to refer to certain positions within the non-toxic *Pseudomonas* exotoxin A sequence (e.g., deletion of Glu at position 553).

A "chimeric protein" or a "chimeric polynucleotide" is an artificially constructed protein or polynucleotide comprising heterologous amino acid sequences or heterologous nucleic acid sequences, respectively.

The term "heterologous" when used with reference to a protein or a nucleic acid indicates that the protein or the nucleic acid comprises two or more sequences or subsequences which are not found in the same relationship to each other in nature. For instance, the nucleic acid is typically recombinantly produced, having two or more sequences from unrelated genes arranged to make a new functional nucleic acid. For example, in one embodiment, the nucleic acid has a promoter from one gene arranged to direct the expression of a coding sequence from a different gene. Thus, with reference to the coding sequence, the promoter is heterologous. Similarly, a sequence from a *Pseudomonas* exotoxin A is heterologous with reference to a Type IV pilin loop sequence when the two sequences are placed in a relationship other than the naturally occurring relationship of the nucleic acids in the genome.

"Type IV pili" refers to filamentous structures covering many gram-negative bacteria, yeast and other microorganisms. The pili on the surface of a microorganism adhere to epithelial cells. In particular, the pili of *Pseudomonas* or *Candida* bind to epithelial cells through specific interaction with asialoGM1 receptors. Type IV pili are primarily composed of protein pilins, which are polymers arranged in a helical bundle. For example, pili of *Pseudomonas aeruginosa* have an average length of 2.5 μm and consist of a single protein with a molecular mass of around 15,000 (Paranchych et al., *Am. Soc. Microbio.* 343–351 (1990)).

The term "Type IV pilin" as used herein refer to pilins that contain a conserved amino terminal hydrophobic domain beginning with an amino-terminal phenylalanine that is methylated upon processing and secretion of the pilin. Another characteristic feature of Type IV pilins is that in the propilin form they contain similar six- or seven-amino acid long leader peptides, which are much shorter than typical signal sequences. Type IV pilins are expressed by several bacterial genuses, including *Neisseria*, *Moraxella*, *Bacteroides*, *Pasteurella* and *Pseudomonas*, *E. coli*, and yeast such as *Candida*. Species within these genuses which express Type IV pilins are, for example, *P. aeruginosa*, *N. gonorrhoeae*, *N. meningtidis*, *Pasteurella multocida*, *M. bovis*, *B. nodosus*. As used herein, the term "Type IV pilin" also includes the Tcp pilin of *Vibrio*, (e.g., *V. cholera*), that is highly homologous to the Type IV pilins of other genuses. Tcp pilin contains the characteristic amino-terminal hydrophobic domain as well as having a modified N-terminal amino acid that in this case may be a modified methionine because the Tcp pilin gene encodes a methionine residue at the position where all the others encode a phenylalanine. Precursor TcpA contains a much longer leader sequence than typical Type IV propilins but retains homology in the region surrounding the processing site. Generally, a pilin protein comprises a region at the N-terminus that is highly conserved, with the rest of the protein containing moderately conserved and hypervariable regions (Paranchych et al., supra). A characteristic feature of all pilins is an intrachain disulfide loop at the C-terminus of the pilin.

The amino acid sequences and nucleic acid sequences of Type IV pilins of various microorganisms are known in the art. See, e.g., NCBI Database Accession No. M14849, J02609 for *Pseudomonas* PAK strain; NCBI Database Accession No. AAC60462 for *Pseudomonas* T2A strain; NCBI Database Accession No. M11323 for *Pseudomonas* PAO strain; NCBI Database Accession No. P17837 for *Pseudomonas* CD strain; NCBI Database Accession No. B31105 for *Pseudomonas* P1 strain; NCBI Database Accession No. Q53391 for *Pseudomonas* KB7 strain; NCBI Database Accession No. AAC60461 for *Pseudomonas* 577B strain; NCBI Database Accession No. A33105 for *Pseudomonas* K122-4 strain; NCBI Database Accession Nos. Z49820, Z69262, and Z69261 for *N. meningtidis*; NCBI Database Accession Nos. X66144 and AF043648 for *N. gonorrhoeae*; NCBI Database Accession Nos. U09807 and X64098 for *V. cholera*; NCBI Database Accession No. AF154834 for *Pasteurella multocida*.

A "Type IV pilin loop sequence" refers to the sequence that forms an intrachain disulfide loop at the C-terminus of the pilin. This region is physically exposed at the tip of the pilus, and interacts with epithelial cell receptors. A Type IV pilin loop sequence as used herein can refer to a sequence between the two cysteine residues that form an intrachain disulfide loop at the C-terminus of the pilin (i.e., excluding the cysteine residues), or a sequence that includes both cysteine residues and amino acids between the two cysteine residues. Depending on whether the site of insertion within non-toxic *Pseudomonas* exotoxin A sequences has cysteine residues, the Type IV pilin loop sequence with or without the flanking cysteine residues can be used to make chimeric proteins of the invention. Examples of Type IV pilin loop sequence are shown as SEQ ID NOS: 3 to 20.

The term "immunogenic fragment thereof" or "immunogenic portion thereof" refers to a polypeptide comprising an epitope that is recognized by cytotoxic T lymphocytes, helper T lymphocytes or B cells.

"Polyclonal antisera" refers to sera comprising polyclonal antibodies against an immunogen, which sera is obtained from a host immunized with the immunogen (e.g., a chimeric protein of the present invention).

Polyclonal antisera that "reduce adherence" of a microorganism expressing a Type IV pilin loop sequence refer to polyclonal antisera that reduce adherence of the microorganism by about 10%, 20%, 30%, 40%, 50%, 60%, 70%, 80%, 90% or 100%, compared to a control. A control can be a prebleed or sera that is not exposed to the chimeric proteins of the present invention.

The term polyclonal antisera that "neutralize cytotoxicity" of *Pseudomonas* exotoxin A in the context of the present invention refer to the ability of antisera to reduce the inhibition of protein synthesis by *Pseudomonas* exotoxin A. Typically, polyclonal antisera can reduce inhibition of protein synthesis by *Pseudomonas* exotoxin A by at least about 30%, more typically at least about 50%, more typically at least about 80%, even more typically at least about 90%, 95%, or 99% compared to a control. A control can be a prebleed or sera that is not exposed to the chimeric proteins of the present invention.

"Nucleic acid" or "polynucleotide" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res*. 19:5081 (1991); Ohtsuka et al., *J. Biol. Chem*. 260:2605–2608 (1985); Rossolini et al., *Mol. Cell. Probes* 8:91–98 (1994)). The term nucleic acid is used interchangeably with gene, cDNA, mRNA, oligonucleotide, and polynucleotide.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" apply to both amino acid and nucleic acid sequences. With respect to particular nucleic acid sequences, conservatively modified variants refer to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid.

Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)

(see, e.g., Creighton, *Proteins* (1984)).

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5–10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, optionally 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency.

An "expression cassette" refers to a polynucleotide molecule comprising expression control sequences operatively linked to coding sequence(s).

A "vector" is a replicon in which another polynucleotide segment is attached, so as to bring about the replication and/or expression of the attached segment.

"Control sequence" refers to polynucleotide sequences which are necessary to effect the expression of coding sequences to which they are ligated. The nature of such control sequences differs depending upon the host organism; in prokaryotes, such control sequences generally include promoter, ribosomal binding site, and terminators; in eukaryotes, generally, such control sequences include promoters, terminators and, in some instances, enhancers. The term "control sequences" is intended to include, at a minimum, all components whose presence is necessary for expression, and may also include additional components whose presence is advantageous, for example, leader sequences.

"Operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences.

A "ligand" is a compound that specifically binds to a target molecule.

A "receptor" is compound that specifically binds to a ligand.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kDa) and one "heavy" chain (about 50–70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$—$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552–554 (1990)).

For preparation of monoclonal or polyclonal antibodies, any technique known in the art can be used (see, e.g., Kohler & Milstein, *Nature* 256:495–497 (1975); Kozbor et al., *Immunology Today* 4: 72 (1983); Cole et al., pp. 77–96 in *Monoclonal Antibodies and Cancer Therapy* (1985)). Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., *Nature* 348:552–554 (1990); Marks et al., *Biotechnology* 10:779–783 (1992)).

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, polyclonal antibodies raised to fusion proteins can be selected to obtain only those polyclonal antibodies that are specifically immunoreactive with fusion protein and not with individual components of the fusion proteins. This selection may be achieved by subtracting out antibodies that cross-react with the individual antigens. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988), for a description of immunoassay formats and conditions that can be used to determine specific immunoreactivity). Typically a specific or selective reaction will be at least twice background signal or noise and more typically more than 10 to 100 times background.

Polynucleotides may comprise a native sequence (i.e., an endogenous sequence that encodes an individual antigen or a portion thereof) or may comprise a variant of such a sequence. Polynucleotide variants may contain one or more substitutions, additions, deletions and/or insertions such that the biological activity of the encoded chimeric protein is not diminished, relative to a chimeric protein comprising native antigens. Variants preferably exhibit at least about 70% identity, more preferably at least about 80% identity and most preferably at least about 90% identity to a polynucleotide sequence that encodes a native polypeptide or a portion thereof.

The terms "identical" or percent "identity," in the context of two or more nucleic acids or polypeptide sequences, refer to two or more sequences or subsequences that are the same or have a specified percentage of amino acid residues or nucleotides that are the same (i.e., 70% identity, optionally 75%, 80%, 85%, 90%, or 95% identity over a specified region), when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence. Optionally, the identity exists over a region that is at least about 25 to about 50 amino acids or nucleotides in length, or optionally over a region that is 75–100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 25 to 500, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J. Mol. Evol.* 35:351–360 (1987). The method used is similar to the method described by Higgins & Sharp, *CABIOS* 5:151–153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nuc. Acids Res.* 12:387–395 (1984)).

Another example of algorithm that is suitable for determining percent sequence identity and sequence similarity are the BLAST and BLAST 2.0 algorithms, which are described in Altschul et al., *Nuc. Acids Res.* 25:3389–3402 (1977) and Altschul et al., *J. Mol. Biol.* 215:403–410 (1990), respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. A cad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

"Immunogen" refers to an entity that induces antibody production in the host animal.

"Vaccine" refers to an agent or composition containing an agent effective to confer a therapeutic degree of immunity on an organism while causing only very low levels of morbidity or mortality. Vaccines and methods for making vaccines are useful in the study of the immune system and in preventing and treating animal or human disease.

An "immunogenic amount" or "immunologically effective amount" is an amount effective to elicit an immune response in a subject.

"Substantially pure" or "isolated" means an object species is the predominant species present (i.e., on a molar basis, more abundant than any other individual macromolecular species in the composition), and a substantially purified fraction is a composition wherein the object species comprises at least about 50% (on a molar basis) of all macromolecular species present. Generally, a substantially pure composition means that about 80% to 90% or more of the macromolecular species present in the composition is the purified species of interest. The object species is purified to essential homogeneity (contaminant species cannot be detected in the composition by conventional detection methods) if the composition consists essentially of a single macromolecular species. Solvent species, small molecules (<500 Daltons), stabilizers (e.g., BSA), and elemental ion species are not considered macromolecular species for purposes of this definition. "Naturally-occurring" as applied to an object refers to the fact that the object can be found in nature. For example, a polypeptide or polynucleotide sequence that is present in an organism (including viruses) that can be isolated from a source in nature and which has not been intentionally modified by man in the laboratory is naturally-occurring.

A "host" refers to any animal including human or non-human animals, such as rodents (e.g., mice or rats), primates, sheep, pigs, guinea pigs, etc.

"Treatment" refers to prophylactic treatment or therapeutic treatment.

A "prophylactic" treatment is a treatment administered to a host who does not exhibit signs of a disease or exhibits only early signs for the purpose of decreasing the risk of developing pathology.

A "therapeutic" treatment is a treatment administered to a host who exhibits signs of pathology for the purpose of diminishing or eliminating those signs.

DESCRIPTION OF THE SPECIFIC EMBODIMENTS

I. Chimeric Proteins Comprising a Non-Toxic *Pseudomonas* Exotoxin a Sequence and a Type IV Pilin Loop Sequence In one aspect, the invention provides a chimeric protein comprising: a non-toxic *Pseudomonas* exotoxin A sequence and a Type IV pilin loop sequence, the Type IV pilin loop sequence being located within the non-toxic *Pseudomonas* exotoxin A sequence, wherein the chimeric protein is capable of reducing the adhesion or adherence of a microorganism expressing the Type IV pilin loop sequence to epithelial cells, and further wherein the chimeric protein, when introduced into a host, is capable of generating polyclonal antisera that reduce adherence of the microorganism expressing the Type IV pilin loop sequence to the epithelial cells. In some embodiments, the chimeric proteins of the invention, when introduced into a host, are also capable of generating polyclonal antisera that neutralize cytotoxicity of *Pseudomonas* exotoxin A. In another aspect, the invention provides a chimeric protein comprising: (a) a non-toxic *Pseudomonas* exotoxin A sequence comprising domain Ia, domain II, and domain III; and (b) a Type IV pilin loop sequence, wherein the Type IV pilin loop sequence is located between domain II and domain III of the non-toxic *Pseudomonas* exotoxin A sequence. In some embodiments, the chimeric protein comprises a non-toxic *Pseudomonas* exotoxin A sequence including domains Ia, II, and III in the native organization structure, except that a Type IV pilin loop sequence, partially or completely, replaces domain Ib and is located between domain II and domain III. Alternatively or additionally, in some embodiments, the chimeric protein comprises a Type IV pilin loop sequence in domain II, replacing amino acids 265 to 287. The nature of non-toxic *Pseudomonas* exotoxin A sequences, various domains of non-toxic *Pseudomonas* exotoxin A sequences, Type IV pilin loop sequences, and their physical relationship within chimeric proteins of the invention are described in detail below.

A. Non-toxic *Pseudomonas* Exotoxin A Sequences

As described in the Definition section above, *Pseudomonas* exotoxin A or PE is secreted by *Pseudomonas aeruginosa* and comprises three prominent domains (Ia, II, and III) and one small subdomain (Ib) connecting domains II and III. In nature, domain Ia of PE, spanning amino acids 1–252, mediates cell binding. Domain II, spanning amino acids 253–364, mediates translocation of the protein to the cytosol. Domain Ib, spanning amino acids 365–399, has no known function. Domain III, spanning amino acids 400–613, is responsible for cytotoxicity and includes an endoplasmic reticulum retention sequence. It also contains sequences that mediates ADP ribosylation of elongation of factor 2 ("EF2"), which inactivates protein synthesis and thus rendering PE to be toxic to cells. Thus, domain Ia or its variant that mediates cell binding is referred to as "a cell recognition domain." Domain II or its variant that mediates translocation of the proteins to the cytosol is referred to as "a translocation domain." Domain III or its variant that functions in translocating the protein from the endosome to the endoplasmic reticulum is referred to as "an endoplasmic reticulum retention domain."

A non-toxic *Pseudomonas* exotoxin A sequence refers to any *Pseudomonas* exotoxin A sequence that lacks ADP ribosylation activity. Generally, a non-toxic *Pseudomonas* exotoxin A sequence has one or more domains or portions of domains with certain biological activities. For example, a non-toxic *Pseudomonas* exotoxin A sequence may comprise a translocation domain (e.g., domain II of *Pseudomonas* exotoxin A) and an endoplasmic reticulum domain (e.g., detoxified domain III of *Pseudomonas* exotoxin A without ADP ribosylation activity). In another example, a non-toxic *Pseudomonas* exotoxin A sequence may be constructed by eliminating amino acids 1–252 yielding a construct referred to as "PE40". In another example, a non-toxic *Pseudomonas* exotoxin A sequence may be constructed by eliminating amino acids 1–279 yielding a construct referred to as "PE37." (See Pastan et al., U.S. Pat. No. 5,602,095.).

Optionally, a cell recognition domain of *Pseudomonas* exotoxin A (e.g., domain I) or other cell recognition domains unrelated to *Pseudomonas* exotoxin A can be included in the present chimeric proteins. A cell recognition domain can be linked, directly or indirectly, to the rest of the chimeric protein. For example, one can ligate sequences encoding a cell recognition domain to the 5' end of non-toxic versions of PE40 or PE37 constructs, which further comprise a Type IV pilin loop sequence.

1. Translocation Domain

The chimeric proteins of the invention comprise a non-toxic *Pseudomonas* exotoxin A sequence comprising a "PE translocation domain." The PE translocation domain comprises an amino acid sequence sufficient to effect translocation of chimeric proteins that have been endocytosed by the cell into the cytosol. The amino acid sequence is identical to, or substantially identical to, a sequence selected from domain II of PE.

The amino acid sequence sufficient to effect translocation can be derived from the translocation domain of native PE. This domain spans amino acids 253–364. The translocation domain can include the entire sequence of domain II. However, the entire sequence is not necessary for translocation. For example, the amino acid sequence can minimally contain, e.g., amino acids 280–344 of domain II of PE. Sequences outside this region, i.e., amino acids 253–279 and/or 345–364, can be eliminated from the domain. This domain can also be engineered with substitutions so long as translocation activity is retained.

The translocation domain functions as follows. After binding to a receptor on the cell surface, the chimeric proteins enter the cell by endocytosis through clathrin-coated pits. Residues 265 and 287 are cysteines that form a disulfide loop. Once internalized into endosomes having an acidic environment, the peptide is cleaved by the protease furin between Arg279 and Gly280. Then, the disulfide bond is reduced. A mutation at Arg279 inhibits proteolytic cleavage and subsequent translocation to the cytosol. Ogata et al., *J. Biol. Chem.* 265:20678–85 (1990). However, a fragment of PE containing the sequence downstream of Arg279 (called "PE37") retains substantial ability to translocate to the cytosol. Siegall et al., *J. Biol. Chem.* 264:14256–61 (1989). Sequences in domain II beyond amino acid 345 also can be deleted without inhibiting translocation. Furthermore, amino acids at positions 339 and 343 appear to be necessary for translocation. Siegall et al., *Biochemistry* 30:7154–59 (1991).

Methods for determining the functionality of a translocation domain are described below in the section on testing.

2. ER Retention Domain

The chimeric protein of the invention can also comprise an amino acid sequence encoding an "endoplasmic reticulum retention domain" as part of a non-toxic exotoxin A sequence. The endoplasmic reticulum ("ER") retention domain functions in translocating the chimeric protein from the endosome to the endoplasmic reticulum, from where it is transported to the cytosol. The ER retention domain is located at the position of domain III in PE. The ER retention domain comprises an amino acid sequence that has, at its carboxy terminus, an ER retention sequence. The ER retention sequence in native PE is REDLK (SEQ ID NO:21). Lysine can be eliminated (i.e., REDL (SEQ ID NO:22)) without a decrease in activity. REDLK (from SEQ ID NO:21) can be replaced with other ER retention sequences, such as KDEL (SEQ ID NO:23), or polymers of these sequences. See Ogata et al., *J. Biol. Chem.* 265:20678–85 (1990); Pastan et al., U.S. Pat. No. 5,458,878; Pastan et al., *Annu. Rev. Biochem.* 61:331–54 (1992).

Sequences up-stream of the ER retention sequence can be the native PE domain III (preferably de-toxified), can be entirely eliminated, or can be replaced by another amino acid sequence. If replaced by another amino acid sequence, the sequence can, itself, be highly immunogenic or can be slightly immunogenic. Activity of this domain can be assessed by testing for translocation of the protein into the target cell cytosol using the assays described below.

In native PE, the ER retention sequence is located at the carboxy terminus of domain III. Domain III has two functions in PE. It exhibits ADP-ribosylating activity and directs endocytosed toxin into the endoplasmic reticulum. Eliminating the ER retention sequence from the chimeric protein does not alter the activity of *Pseudomonas* exotoxin as a superantigen, but does inhibit its utility to elicit an MHC Class I-dependent cell-mediated immune response.

The ribosylating activity of PE is located between about amino acids 400 and 600 of PE. In methods of vaccinating a host using the chimeric proteins of this invention, it is preferable that the protein be non-toxic. One method of doing so is by eliminating ADP ribosylation activity. In this way, the chimeric protein can function as a vector for Type IV pilin loop sequences to be processed by the cell and presented on the cell surface with MHC Class I molecules, rather than as a toxin. ADP ribosylation activity can be eliminated by, for example, deleting amino acid E553 ("ΔE553") of the native PE. See, e.g., Lukac et al., *Infect. and Immun.* 56:3095–3098 (1988). In another example, substitution of histidine residue of PE at 426 with a tyrosine residue also inactivates the ADP-ribosylation of PE (see Kessler & Galloway, supra). Other amino acids in domain III can be modified from the protein to eliminate ADP ribosylation activity. An ER retention sequence is generally included at the carboxy-terminus of the chimeric protein.

In one embodiment, the sequence of the ER retention domain is substantially identical to the native amino acid sequences of the domain III, or a fragment of it. In some embodiments, the ER retention domain is domain m of PE.

In another embodiment, a cell recognition domain is inserted into the amino acid sequence of the ER retention domain (e.g., into domain III). For example, the cell recognition domain can be inserted just up-stream of the ER retention sequence, so that the ER retention sequence is connected directly or within ten amino acids of the carboxy terminus of the cell recognition domain.

B. Cell Recognition Domain

Optionally, the chimeric protein of the invention can comprise an amino acid sequence encoding a "cell recognition domain." The cell recognition domain functions as a ligand for a cell surface receptor. It mediates binding of the protein to a cell. It can be used to target the chimeric protein to a cell which will transport it to the cytosol for processing. A cell recognition domain may not be necessarily included in the chimeric protein, as a Type IV pilin loop sequence within the chimeric protein targets receptors on epithelial cells.

The cell recognition domain functions to attach the chimeric protein to a target cell, and it can be any suitable material, e.g., a polypeptide known to a particular receptor in the target cell. For example, the cell recognition domain generally has the size of known polypeptide ligands, e.g., between about 10 amino acids and about 1500 amino acids, or about 100 amino acids and about 300 amino acids. Several methods are useful for identifying functional cell recognition domains for use in chimeric proteins. One method involves detecting binding between a chimeric protein that comprises the cell recognition domain with the receptor or with a cell bearing the receptor. Other methods involve detecting entry of the chimeric protein into the cytosol, indicating that the first step, cell binding, was successful. These methods are described in detail below in the section on testing.

In one embodiment, the cell recognition domain is domain Ia of PE, thereby targeting the chimeric protein to the α2-MR domain. In other embodiments domain Ia can be substituted with ligands that bind to cell surface receptors or antibodies or antibody fragments directed to cell surface receptors. For example, to target epithelial cells, a cell binding domain can be a ligand for or antibodies against the EGF receptor, transferrin receptors, interleukin-2 receptors, interleukin-6 receptors, interleukin-8 receptors, or Fc receptors, or poly-IgG receptors. To target liver cells, a cell binding domain can be, e.g., a ligand for or antibodies against asialoglycoprotein receptors. To target T cells, a cell binding domain can be, e.g., a ligand for or antibodies against CD3, CD4, CD8, or chemokine receptors. To target activated T-cells and B-cells, a cell binding domain can be, e.g., a ligand for or antibodies against CD25. To target dendritic cells, a cell binding domain can be, e.g., ligands for or antibodies against CD11B, CD11C, CD80, and CD86 MHC class I and II. To target macrophages, a cell binding domain can be, e.g., ligands for or antibodies against TNFalpha receptors, chemokine receptors, TOLL receptors, M-CSF receptors, GM-CSF receptors, scavenger receptors, and Fc receptors. To target endothelial cells, a cell binding domain can be, e.g., a ligand for or antibodies against VEGF receptors. Also, cytokine receptors which are found in many cell types can be targeted. Pastan et al. *Ann. Rev. Biochem.* 61:331–54 (1992).

The cell recognition domain can be located at any suitable position within the present chimeric proteins. For example, the cell recognition domain can be located in the N-terminus of the chimeric protein (e.g., position equivalent to domain Ia of non-toxic PE). However, this domain can be moved out of the normal organizational sequence of exotoxin A. More particularly, the cell recognition domain can be inserted upstream of the ER retention domain. Alternatively the cell recognition domain can be chemically coupled to the rest of the chimeric protein. Also, the chimeric protein can include a first cell recognition domain at the location of the Ia domain and a second cell recognition domain upstream of the ER retention domain. Such constructs can bind to more than one cell type. See, e.g., Kreitman et al., *Bioconjugate Chem.* 3:63–68 (1992). For example, TGFα has been inserted into domain III just before amino acid 604, i.e., about ten amino acids from the carboxy-terminus. This chimeric protein binds to cells bearing EGF receptor. Pastan et al., U.S. Pat. No. 5,602,095.

The cell recognition domain can be inserted or attached to the rest of the chimeric proteins using any suitable methods. For example, the domain can be attached to the rest of the chimeric protein directly or indirectly using a linker. The linker can form covalent bonds or high-affinity non-covalent bonds. Suitable linkers are well known to those of ordinary skill in the art. In another example, the cell recognition domain is expressed as a single chimeric polypeptide from a nucleic acid sequence encoding the single contiguous chimeric protein.

C. Type IV Pilin Loop Sequences

The chimeric protein also comprises a Type IV pilin loop sequence within a non-toxic *Pseudomonas* exotoxin A sequence. The Type IV pilin loop sequence is generally derived from a sequence that forms an intrachain disulfide loop at the C-terminus of the pilin protein. The Type IV pilin loop sequence allows the chimeric protein to react with asialoGM1 receptors on epithelial cells. This loop is dominated by main chain residues. Therefore, pilins from several strains bind the same receptor despite sequence variation and the difference in length (e.g., for certain *Pseudomonas* strains, 12 and 17 amino acid loops (or 14 to 19 amino acids including flanking cysteine residues)). A Type IV loop pilin sequence comprises at least about 5 amino acid residues, typically between about 10 to 100 amino acids, more typically about 12 to 70 amino acids, even more typically about 12 to 20 amino acids. Embodiments of the invention can have one unit of the Type IV pilin loop sequence or multiple repeating units (e.g., 2, 3, 4, etc.) of the same or different Type IV pilin loop sequences. In some embodiments, the chimeric proteins comprise more than one Type IV pilin loop sequences at different locations.

A Type IV pilin loop sequence can be derived from any microorganism that adhere to epithelial cells. For example, a Type IV pilin sequence can be derived from bacteria or yeast, such as *Pseudomonas aeruginosa, Neisseria meningtidis, Neisseria gonorrhoeae, Vibro cholera, Pasteurella multocidam* or *Candida*. Examples of a Type IV pilin sequence are shown as SEQ ID NOS: 3 to 20.

Type IV pilin sequences from different *Pseudomonas aeruginosa* strains vary in terms of their sequence as well as their length. Several *Pseudomonas aeruginosa* strains have a short pilin loop consisting of 14 amino acids (from cysteine 129 to cysteine 142) as shown in Table I below. Other *Pseudomonas aeruginosa* strains have a long pilin loop consisting of 19 amino acids (from cysteine 133 to 151) as shown in Table 2 below.

TABLE 1

| P. aeruginosa strains (with a short pilin loop) | Type IV pilin loop sequence (Cysteine 129 to Cysteine 142) | |
|---|---|---|
| PAK | CTSDQDEQFIPKGC | (SEQ ID NO:3) |
| T2A | CTSTQDEMFIPKGC | (SEQ ID NO:4) |
| PAO, 90063 | CKSTQDPMFTPKGC | (SEQ ID NO:5) |
| CD, PA103 | CTSTQEEMFIPKGC | (SEQ ID NO:6) |
| K122-4 | CTSNADNKYLPKTC | (SEQ ID NO:7) |
| KB7, 82932, 82935 | CATTVDAKFRPNGC | (SEQ ID NO:8) |
| 1071 | CESTQDPMFTPKGC | (SEQ ID NO:9) |

TABLE 2

| P. aeruginosa strains (with a long pilin loop) | Type IV pilin loop sequence (Cysteine 133 to Cysteine 151) | |
|---|---|---|
| 577B | CNITKTPTAWKPNYAPANC | (SEQ ID NO:10) |
| 1244, 9D2, P1 | CKITKTPTAWKPNYAPANC | (SEQ ID NO:11) |
| SBI-N | CGITGSPTNWKANYAPANC | (SEQ ID NO:12) |

Type IV pilin loop sequences from microorganisms other than *P. aeruginosa* can also be included in the chimeric proteins of the invention. Examples of Type IV pilin loop amino acid sequences from other microorganisms are shown in Table 3 below.

TABLE 3

| Microorganism | Type IV pilin loop sequence | |
|---|---|---|
| *Neisseria meningtidis* (Z49820) | CGLPVARDDTDSATDVKADTTDNINTKHLPSTC | (SEQ ID NO:13) |
| *Neisseria meningtidis* (Z69262) | CGQPVTRGAGNAGKADDVTKAGNDNEKINTKHLPSTC | (SEQ ID NO:14) |
| *Neisseria meningtidis* (Z69261) | CGQPVTRAKADADAAGKDTTNIDTKHLPSTC | (SEQ ID NO:15) |
| *Neisseria gonorrhoeae* (pilE; X66144) | CGQPVTRTGDNDDTVADAKDGKEIDTKHLPSTC | (SEQ ID NO:16) |
| *Neisseria gonorrhoeae* (pilE; AF043648) | CGQPVKRDAGAKTGADDVKADGNNGINTKHLPSTC | (SEQ ID NO:17) |
| *Vibrio cholera* (U09807) | CKTLVTSVGDMFPFINVKEGAFAAVADLGDFETSVADAATGAGVIKSIAPGSANLNLTNITHVEKLC | (SEQ ID NO:18) |
| *Vibrio cholera* (X64098) | CKTLITSVGDMFPYIAIKAGGAVALADLGDFENSAAAAETGVGVIKSIAPASKNLDLTNITHVEKLC | (SEQ ID NO:19) |
| *Pasteurella multocida* (AF154834) | CNGGSEVFPAGFC | (SEQ ID NO:20) |

One of skill in the art will recognize that the above described Type IV pilin sequences are merely exemplary and that other Type IV pilin sequences can be readily inserted into the chimeric proteins of the present invention. For example, Type IV pilin loop sequences described in, e.g., U.S. Pat. No. 5,612,036 (Hodges et al.) can also be incorporated into the chimeric proteins of the present invention.

The Type IV pilin loop sequence can be located at any suitable position within the chimeric protein of the invention. In one embodiment, the Type IV pilin sequence is inserted between the translocation domain (e.g., domain II of non-toxic exotoxin A) and the ER retention domain (e.g., domain III of non-toxic exotoxin A). In another embodiment, the chimeric protein has the basic organization structure of non-toxic *Pseudomonas* exotoxin A including domain Ia, domain II, domain Ib, and domain III, except that domain Ib is, partially or completely, replaced by the Type IV pilin loop sequence. In native *Pseudomonas* exotoxin A, domain Ib spans amino acids 365 to 399. The native Ib domain is structurally characterized by a disulfide bond between two cysteines at positions 372 and 379. Domain Ib is not essential for cell binding, translocation, ER retention or ADP ribosylation activity. Therefore, it can be partially or entirely replaced by a Type IV pilin loop sequence. For example, a Type IV pilin loop sequence can be inserted between the two cysteines at positions 372 and 379, replacing the 6 amino acid residues between the two cysteines. In another embodiment, the Type IV pilin loop sequence can be inserted into the Ib domain without removing any of the Ib domain sequences. In another embodiment, the Type IV pilin loop sequence can be positioned in another location which forms a cysteine-cysteine disulfide bonded loop, such as amino acids 265–287 of domain II of non-toxic *Pseudomonas* exotoxin A. In some embodiments, more than one Type IV pilin loop sequences can be inserted into different locations within the chimeric protein.

Depending on whether the site of insertion within a non-toxic *Pseudomonas* exotoxin A sequence has cysteine residues, a Type IV pilin loop sequence with or without cysteine residues at the N- and C-termini can be used. For example, if the site of insert in the non-toxic *Pseudomonas* exotoxin A sequence does not have cysteine residues, then a Type IV pilin loop sequence with cysteine residues at its termini (e.g., 14 amino acids shown in SEQ ID NO:3) can be inserted. In another example, if a Type IV pilin loop sequence is inserted in the cysteine-cysteine loop of the native Ib domain, replacing the six amino acids between the cysteine residues, then a Type IV pilin loop sequence can be a sequence without terminal cysteines (e.g., 12 amino acids between the two cysteines shown in SEQ ID NO:3). Therefore, a cysteine-cysteine loop can be preferably formed within the chimeric protein of the invention. When the Type IV pilin loop sequence within the chimeric protein is presented as a cysteine-cysteine disulfide bonded loop, the Type IV pilin loop structure may stick out from the rest of the chimeric protein, where it is available to interact with, e.g., asialoGM1 receptors or with immune system components.

II. Chimeric Polynucleotides and Expression of Polynucleotides

A. Polynucleotides Encoding the Chimeric Proteins

In another aspect, the invention provides polynucleotides encoding the chimeric proteins of the invention. Suitable amino acid sequences of non-toxic *Pseudomonas* exotoxin A sequences (e.g., comprising a translocation domain and an ER retention domain), cell recognition domains, and Type IV pilin loop sequences and their physical locations within the present chimeric proteins are described in detail above. Any polynucleotides that encode these amino acid sequences are within the scope of the present invention.

1. Identification of Non-Toxic *Pseudononas* Exotoxin a Sequences

Polynucleotides that encode non-toxic *Pseudomonas* exotoxin A amino acid sequences may be identified, prepared and manipulated using any of a variety of well established techniques. A nucleotide encoding native *Pseudomonas* exotoxin A is shown as SEQ ID NO:1. The practitioner can use this sequence to prepare non-toxic *Pseudomonas* exotoxin A sequences using various cloning and in vitro amplification methodologies known in the art. PCR methods are described in, for example, U.S. Pat. No. 4,683,195; Mullis et al. *Cold Spring Harbor Symp. Quant. Biol.* 51:263 (1987); and Erlich, ed., *PCR Technology*, (Stockton Press, NY, 1989); Dieffenfach & Dveksler, *PCR Primer: A Laboratory Manual* (1995). These primers can be used, e.g., to amplify either the full length sequence, partial sequences or a probe of one to several hundred nucleotides, which is then used to screen cDNA or genomic libraries for related nucleic acid sequence homologs. Polynucleotides can also be isolated by screening genomic or cDNA libraries (e.g., *Pseudomonas aeruginosa*) with probes selected from the sequences of the desired polynucleotide under stringent hybridization conditions.

As an illustration, to clone a *Pseudomonas* exotoxin A sequence comprising all of the domains (domain Ia, domain II, domain Ib, and domain III), the following primers can be used: Forward—GGCCCATATGCACCTGATACCCCAT (SEQ ID NO:24); and Reverse—GAATTCAGTTACT-TCAGGTCCTCG (SEQ ID NO:25). To clone a *Pseudomonas* exotoxin A sequence comprising domain II, domain Ib, and domain III, the following primers can be used: Forward—GGCCCATATGGAGGGCGGCAGCCTGGCC (SEQ ID NO:26); and Reverse—GAATTCAGTTACT-TCAGGTCCTCG (SEQ ID NO:27).

Other *Pseudomonas* exotoxin A constructs that can be used in the embodiments of the invention are also described in, e.g., U.S. Pat. No. 5,602,095 (Pastan et al.). As described in the '095 patent, eliminating nucleotides encoding amino acids 1–252 yields a construct referred to as "PE40." Eliminating nucleotides encoding amino acids 1–279 yields a construct referred to as "PE37." Non-toxic versions of these constructs (which lack domain Ia of native exotoxin A) are particularly useful for ligating them to sequences encoding heterologous cell recognition domains to the 5' end of these constructs. These constructs can optionally encode an amino-terminal methionine.

In addition, *Pseudomonas* exotoxin A can be further modified using site-directed mutagenesis or other techniques known in the art, to alter the molecule for a particular desired application. Means to alter *Pseudomonas* exotoxin A in a manner that does not substantially affect the functional advantages provided by the PE molecules described herein can also be used and such resulting molecules are intended to be covered herein.

Non-toxic *Pseudomonas* exotoxin A sequences can be generated from these *Pseudomonas* exotoxin A sequences by modifying portions of domain III so that they lack ADP ribosylation activity. The ribosylating activity of PE is located between about amino acids 400 and 600 of native *Pseudomonas* exotoxin A. For example, deleting amino acid E553 ("ΔE553") from domain III detoxifies the molecule. This detoxified PE is referred to as "PE ΔE553." Other amino acids within domain III can be modified by, e.g., deletion, substitution or addition of amino acid residues, to eliminate ADP ribosylation activity. For example, substitution of histidine residue of PE at 426 with a tyrosine residue also inactivates the ADP-ribosylation of PE (see Kessler & Galloway, supra).

In some embodiments, non-toxic *Pseudomonas* exotoxin A sequences can be further modified to accommodate cloning sites for insertion of a Type IV pilin loop sequence. For example, a cloning site for the Type IV pilin sequence can be introduced between the nucleotides encoding the cysteines of domain Ib of non-toxic *Pseudomonas* exotoxin A. For example, a nucleotide sequence encoding a portion of the Ib domain between the cysteine-encoding residues can be removed and replaced with a nucleotide sequence encoding an amino acid sequence and that includes a PstI cloning site. This example is described in detail in the Example section. Alternatively, a longer portion of domain Ib or entire domain Ib can be removed and replaced with an amino acid sequence and that includes cloning site(s).

The construct can also be engineered to encode a secretory sequence at the amino terminus of the protein. Such constructs are useful for producing the chimeric proteins in mammalian cells. In vitro, such constructs simplify isolation of the chimeric proteins. In vivo, the constructs are useful as polynucleotide vaccines; cells that incorporate the construct will express the protein and secrete it where it can interact with the immune system.

2. Identification Type IV Pilin Loop Sequences

Polynucleotides that encode Type IV pilin loop amino acid sequences may be identified, prepared and manipulated using any of a variety of well-established techniques. Type IV pilin nucleotide and amino acid sequences from various microorganisms are well-known in the art. See, e.g., NCBI Database Accession No. M14849 J02609 for *Pseudomonas* PAK strain; NCBI Database Accession No. AAC60462 for *Pseudomonas* T2A strain; NCBI Database Accession No. M11323 for *Pseudomonas* PAO strain; NCBI Database Accession No. P17837 for *Pseudomonas* CD strain; NCBI Database Accession No. B31105 for *Pseudomonas* P1 strain; NCBI Database Accession No. Q53391 for *Pseudomonas* KB7 strain; NCBI Database Accession No. AAC60461 for *Pseudomonas* 577B strain; NCBI Database Accession No. A33105 for *Pseudomonas* K122-4 strain; NCBI Database Accession Nos. Z49820, Z69262, and Z69261 for *N. meningtidis*; NCBI Database Accession Nos. X66144 and AF043648 for *N. gonorrhoeae*; NCBI Database Accession Nos. U09807 and X64098 for *V. cholera*; NCBI Database Accession No. AF154834 for *Pasteurella multocida*. The practitioners can clone and identify other pilin nucleotides and amino acid sequences from other microorganisms using various cloning and in vitro amplification methodologies known in the art. For example, to clone other pilin loop *Pseudomonas* strains from a library, primers for amplification from the highly conserved 5' end of the pilin gene and the 3' end of the neighboring gene (Nicotinate-nucleotide pyrophosphorylase) in the *Pseudomonas* genome can be used. Exemplary primers PCR (listed in the 5' to 3' direction) for sequencing the pilin genes are as follows: pilATG (26 nc) GAGATATTCATGAAAGCTCAAAAAGG (SEQ ID NO:28); and nadB4 (20 nc) ATCTCCATCGGCACCCT-GAC (SEQ ID NO:29); or nadB1 (21 nc) TGGAAGTG-GAAGTGGAGAACC (SEQ ID NO:30).

From these Type IV pilin polynucleotides, the portion that forms the C-terminal intrachain disulfide loop (i.e., Type IV pilin loop) can be readily identified visually. Examples of Type IV pilin loop amino acids are shown as SEQ ID NO:3 to 20 in Tables 1–3 above. Any degenerate nucleotides encoding these and other Type IV pilin loop amino acids can be used to construct chimeric polynucleotides of the invention. In some embodiments, to facilitate insertion of Type IV pilin loop sequence into a non-toxic *Pseudomonas* exotoxin A sequence, 5' and/or 3' ends of Type IV pilin loop nucleotide sequence can be modified to incorporate cohesive ends for cloning sites (e.g., PstI).

As described above, typically, a Type IV pilin loop sequence is inserted into domain Ib, or can partially or fully replace domain Ib of non-toxic *Pseudomonas* exotoxin A. In some embodiments, a Type IV pilin loop sequence can be inserted into other suitable locations within a non-toxic *Pseudomonas* exotoxin A sequence. For example, a Type IV pilin loop sequence can be inserted in another location of non-toxic *Pseudomonas* exotoxin A which forms a cysteine-cysteine disulfide bonded loop, such as amino acids 265–287 of domain II of non-toxic *Pseudomonas* exotoxin A. Other suitable locations for insertion can be readily tested using functional tests described herein. In some embodiments, more than one Type IV pilin loop sequences can be inserted into chimeric polynucleotides of the invention (e.g., a first pilin loop sequence in domain Ib and a second pilin loop sequence in domain II).

3. Identification of Cell Recognition Domain

Polynucleotides encoding various cell recognition domains are well-known in the art. As described above, in one embodiment, the cell recognition domain is domain Ia of PE, thereby targeting the chimeric protein to the α2-MR domain. In this embodiment, the cell recognition domain can be readily included in the chimeric polynucleotides using SEQ ID NO:1 as described above. In other embodiments domain Ia can be substituted with ligands that bind to cell surface receptors or antibodies or antibody fragments directed to cell surface receptors. Suitable ligands and antibodies or antibody fragments are described above in section IB above. Suitable locations for insertion of cell recognition domain into chimeric proteins and chimeric polynucleotides are also described above in section IB.

The cell recognition domain can be inserted or attached to the rest of the chimeric proteins using any suitable methods. For example, the domain can be attached to the rest of the chimeric protein directly or indirectly using a linker. The linker can form covalent bonds or high-affinity non-covalent bonds. Suitable linkers are well known to those of ordinary skill in the art. In another example, the cell recognition domain is expressed as a single chimeric polypeptide from a nucleic acid sequence encoding the single contiguous chimeric protein.

B. Expression Cassettes and Vectors

Embodiments of the invention also provide expression cassettes and vectors for expressing the present chimeric proteins. Expression cassettes are recombinant polynucleotide molecules comprising expression control sequences operatively linked to a polynucleotide encoding the chimeric protein. Expression vectors comprise these expression cassettes in addition to other sequences necessary for replication in cells.

Expression vectors can be adapted for function in prokaryotes or eukaryotes by inclusion of appropriate promoters, replication sequences, markers, etc. for transcription and translation of mRNA. The construction of expression vectors and the expression of genes in transfected cells involves the use of molecular cloning techniques also well known in the art. Sambrook et al., Molecular Cloning—A Laboratory Manual, Cold Spring Harbor Laboratory, Cold Spring Harbor, N.Y., (1989) and Current Protocols in Molecular Biology, F. M. Ausubel et al., eds., (Current Protocols, a joint venture between Greene Publishing Associates, Inc. and John Wiley & Sons, Inc.). Useful promoters for such purposes include a metallothionein promoter, a constitutive adenovirus major late promoter, a dexamethasone-inducible MMTV promoter, a SV40 promoter, a MRP polIII promoter, a constitutive MPSV promoter, a tetracycline-inducible CMV promoter (such as the human immediate-early CMV promoter), and a constitutive CMV promoter. A plasmid useful for gene therapy can comprise other functional elements, such as selectable markers, identification regions, and other genes.

Expression vectors useful in this invention depend on their intended use. Such expression vectors must contain expression and replication signals compatible with the host cell. Expression vectors useful for expressing the chimeric proteins include viral vectors such as retroviruses, adenoviruses and adeno-associated viruses, plasmid vectors, cosmids, and the like. Viral and plasmid vectors are preferred for transfecting mammalian cells. The expression vector pcDNA1 (Invitrogen, San Diego, Calif.), in which the expression control sequence comprises the CMV promoter, provides good rates of transfection and expression. Adeno-associated viral vectors are useful in the gene therapy methods of this invention.

A variety of means are available for delivering polynucleotides to cells including, for example, direct uptake of the molecule by a cell from solution, facilitated uptake through lipofection (e.g., liposomes or immunoliposomes), particle-mediated transfection, and intracellular expression from an expression cassette having an expression control sequence operably linked to a nucleotide sequence that encodes the inhibitory polynucleotide. See also Inouye et al., U.S. Pat. No. 5,272,065; Methods in Enzymology, vol. 185, Academic Press, Inc., San Diego, Calif. (D. V. Goeddel, ed.) (1990) or M. Krieger, Gene Transfer and Expression—A Laboratory Manual, Stockton Press, New York, N.Y., (1990). Recombinant DNA expression plasmids can also be used to prepare the polynucleotides of the invention for delivery by means other than by gene therapy, although it may be more economical to make short oligonucleotides by in vitro chemical synthesis.

The construct can also contain a tag to simplify isolation of the protein. For example, a polyhistidine tag of, e.g., six histidine residues, can be incorporated at the amino terminal end of the protein. The polyhistidine tag allows convenient isolation of the protein in a single step by nickel-chelate chromatography.

C. Recombinant Cells

The invention also provides recombinant cells comprising an expression cassette or vectors for expression of the nucleotide sequences encoding a chimeric protein of this invention. Host cells can be selected for high levels of expression in order to purify the protein. The cells can be prokaryotic cells, such as *E. coli*, or eukaryotic cells. Useful eukaryotic cells include yeast and mammalian cells. The cell can be, e.g., a recombinant cell in culture or a cell in vivo.

*E. coli* has been successfully used to produce the chimeric proteins of the present invention. The protein can fold and disulfide bonds can form in this cell.

D. Chimeric Protein Purification and Preparation

Once a recombinant chimeric protein is expressed, it can be identified by assays based on the physical or functional properties of the product, including radioactive labeling of the product followed by analysis by gel electrophoresis, radioimmunoassay, ELISA, bioassays, etc.

Once the encoded protein is identified, it may be isolated and purified by standard methods including chromatography (e.g., high performance liquid chromatography, ion exchange, affinity, and sizing column chromatography), centrifugation, differential solubility, or by any other standard technique for the purification of proteins. See, generally, R. Scopes, *Protein Purification*, Springer-Verlag, N.Y. (1982), Deutscher, *Methods in Enzymology Vol. 182: Guide to Protein Purification*, Academic Press, Inc. N.Y. (1990). The actual conditions used will depend, in part, on factors such as net charge, hydrophobicity, hydrophilicity, etc., and will be apparent to those having skill in the art.

After biological expression or purification, the chimeric proteins may possess a conformation substantially different than the native conformations of the constituent proteins. In this case, it is helpful to denature and reduce the chimeric protein and then to cause the protein to re-fold into the preferred conformation. Methods of reducing and denaturing polypeptides and inducing re-folding are well known to those of skill in the art (see Debinski et al., *J. Biol. Chem.* 268:14065–14070 (1993); Kreitman & Pastan, *Bioconjug. Chem.* 4:581–585 (1993); and Buchner et al., *Anal. Biochem.* 205:263–270 (1992)). Debinski et al., for example, describe the denaturation and reduction of inclusion body polypeptides in guanidine-DTE. The polypeptide is then refolded in a redox buffer containing oxidized glutathione and L-arginine.

E. Testing Functional Properties of the Chimeric Protein

The functional properties of the chimeric protein as a whole or each component thereof are using various routine assays. For example, the chimeric proteins are tested in terms of cell recognition, cytosolic translocation, Type IV pilin adhesion, and immunogenicity. The entire chimeric protein can be tested, or the function of various domains can be tested by substituting them for native domains of the wild-type exotoxin A.

1. Receptor Binding/Cell Recognition

To determine whether the cell binding domain present in the chimeric protein functions properly, the ability of the chimeric protein to bind to the target receptor (either isolated or on the cell surface) is tested using various methods known in the art.

In one method, binding of the chimeric protein to a target is performed by affinity chromatography. For example, the chimeric protein is attached to a matrix in an affinity column, and binding of the receptor to the matrix detected. Alternatively, the target receptor is attached to a matrix in an affinity column, and binding of the chimeric protein to the matrix is detected.

Binding of the chimeric protein to receptors on cells can be tested by, for example, labeling the chimeric protein and detecting its binding to cells by, e.g., fluorescent cell sorting, autoradiography, etc.

In some embodiments, toxic version of chimeric proteins (which has ADP ribosylation activity) can be used to test whether the cell binding domain of the chimeric proteins binds to its target receptor. For example, the toxic version of chimeric proteins can be incubated with either cells that express the target receptors or cells that do not express the target receptors, and cytotoxic effects of the toxic version of chimeric proteins can be determined (e.g., by measuring inhibition of [$^3$H]leucine incorporation).

If antibodies have been identified that bind to the ligand from which the cell recognition domain is derived, they are also useful to detect the existence of the cell recognition domain in the chimeric protein by immunoassay, or by competition assay for the cognate receptor.

In above testing methods, typically a specific or selective reaction of the chimeric protein to a target will be at least twice background signal or noise and more typically more than 10 to 100 times background.

These methods are described in detail in, e.g., Kreitman et al., *Proc. Natl. Acad. Sci. U.S.A* 87:8291–5 (1990); Siegall et al., *Semin. Cancer Biol.* 1:345–50 (1990); Siegall et al., *Cancer Res.* 50:7786–8 (1990); FitzGerald et al., *J. Cell Biol.* 126(6):1533–41 (1995).

2. Translocation to the Cytosol

To determine whether the translocation domain and the ER retention domain of the chimeric protein properly functions, the ability of the chimeric protein to gain access to the cytosol is tested.

a) Presence in the Cytosol

In one method, access to the cytosol is determined by detecting the physical presence of the chimeric protein in the cytosol. For example, the chimeric protein can be labeled and the chimeric protein exposed to the cell. Then, the cytosolic fraction is isolated and the amount of label in the fraction determined. Detecting label in the fraction indicates that the chimera has gained access to the cytosol. This result can be compared with a control, e.g., background noise or signal. If the detectable label in the cytosolic fraction is at least twice background signal or noise and more typically more than 10 to 100 times background, then, this result indicates that the chimeric protein has gained access to the cytosol.

b) ADP Ribosylation Activity

In another method, the ability of the translocation domain and ER retention domain to effect translocation to the cytosol can be tested with a construct containing a domain III having ADP ribosylation activity. Briefly, cells are seeded in tissue culture plates and exposed to the toxic version of the chimeric protein containing the modified translocation domain or ER retention sequence. ADP ribosylation activity is determined as a function of inhibition of protein synthesis by, e.g., monitoring the incorporation of $^3$H-leucine. This method is further described in detail in FitzGerald at al., *J. Bio. Chem.* 273:9951–9958 (1998). The incorporation of $^3$H-leucine in cells exposed the toxic version of the chimeric protein can be compared to that of a non-toxic counterpart or to background noise. If the incorporation of $^3$H-leucine in cells exposed the toxic version is reduced by at least twice, more typically more than 10 to 100 times that of the non-toxic counterpart (or compared to background noise), then it can be said that the chimeric protein has properly gained entry to the cytosol.

3. Type IV Pilin Loop Adhesion

If the Type IV pilin sequence within the chimeric protein has a structure that is exposed to a solvent and has near-native conformation, the Type IV pilin loop sequence within the chimeric protein should bind to, e.g., asialoGM1 receptors or other receptors on epithelial cells and also compete with microorganisms expressing the Type IV pilin loop sequence for binding to these receptors. Therefore, whether or not the Type IV pilin loop sequence is properly functioning within the chimeric protein is tested by measuring its ability to adhere to epithelial cells or its ability to block adherence of microorganisms expressing a Type IV pilin loop sequence (e.g., *P. aeruginosa*) to epithelial cells. These assays can be readily designed by one of skill in the art.

As an example, if a Type IV pilin loop sequence is derived from *P. aeruginosa* or *Candida,* an adhesion assay can be performed with a substrate coated with asialoGM1. Various concentrations of the chimeric protein comprising Type IV pilin sequence can be assayed for reactivity with immobilized asialoGM1. To determine specificity of this reactivity between the chimeric protein and asialoGM1, a competition assay can be performed. For example, soluble asialoGM1 can be added to interfere the chimeric protein binding to immobilized asialoGM1. This method is described in detail in the example section IIB3. This binding result can be compared to a control (e.g., the same chimeric protein without the pilin loop insert or with a scrambled pilin loop sequence insert). If the amount of binding of the chimeric protein to immobilized asialo GM1 is at least twice, typically about 10 to 100 times greater than the control, then it can be said that the pilin loop insert in the chimeric protein is functioning properly.

In another example, one can test the ability of the chimeric protein to block binding of microorganisms expressing the Type IV pilin loop sequence to epithelial cells. The selection of epithelial cells depends on which microorganism Type IV pilin loop sequence within the chimeric protein is derived from. For instance, if the Type IV pilin loop sequence within the chimeric protein is derived from *V. cholera*, then intestinal epithelial cells can be used binding assays. If the Type IV pilin loop sequence within the chimeric protein is derived from *N. gonorrhoeae*, then epithelial cells of genital urinary system can be used for binding assays. If the Type IV pilin loop sequence within the chimeric protein is derived from *P. aeruginosa*, then lung epithelial cells can be used for binding assays.

As an illustration, various *Pseudomonas aeruginosa* strains that express Type IV pilin can be added different to the human lung epithelial cell line, A549, which will result in the binding of *Pseudomonas aeruginosa* to these cells. Then, the chimeric protein can be added. If the Type IV pilin sequence within the chimeric protein is present in near-native conformation, the chimeric protein would compete with *Pseudomonas aeruginosa* binding and would result in reduction of *Pseudomonas aeruginosa* adherence to the epithelial cells. This method is described in detail in the example section III below. The result from this competition assay can be compared to the result obtained with a control (e.g., the same chimeric protein except without the pilin loop insert or the same chimeric protein with a scrambled pilin loop sequence insert). If the chimeric protein can reduce *Pseudomonas* binding at least twice or typically about 10 to 100 times better than the control, then it can be said that the pilin loop insert in the chimeric protein is functioning properly.

4. Immunogenicity

To determine whether the chimeric protein retains its immunogenicity respect to both parts of the chimeric protein (i.e., a Type IV pilin loop sequence and a non-toxic *Pseudomonas* exotoxin A sequence), properties of the antisera raised against the chimeric protein are tested.

a) Immunogenicity of Type IV Pilin Sequence

Immunogenicity of a Type IV pilin sequence within the chimeric protein is tested by adhesion test using the antisera raised against the chimeric protein. An animal, such as a mouse or a rabbit, can be immunized with a composition comprising the chimeric protein as described below in Example section IVA. The post immunization antisera from the animal can be obtained and prepared to determine if the antisera can inhibit binding of microorganisms expressing the Type IV pilin sequence to the epithelial cells. For example, *Pseudomonas aeruginosa* can be added to the epithelial cells, and the amount of *Pseudomonas* binding to the epithelial cells is determined. Then, the post immunization antisera can be added to the epithelial cells to determine if antisera reduce binding of *Pseudomonas aeruginosa* to the epithelial cells. This assay is described in detail in Example section IVB. If the pilin loop sequence within the chimeric protein is present in near native conformation, then it is expected that antisera raised against the chimeric protein (at a suitable dilution, e.g., 1:10 or 1:100) can reduce *Pseudomonas* binding by at least about 20%, typically at least about 30%, more typically at least about 50%.

b) Toxin Neutralizing Response

Immunogenicity of a non-toxic *Pseudomonas* exotoxin A sequence within the chimeric protein is tested by using antisera raised against the chimeric protein. Specifically, post immunization antisera is tested for its ability to neutralize cytotoxicity of *Pseudomonas* exotoxin A. For example, one can test the inhibition of protein synthesis of purified *Pseudomonas* exotoxin A on eukaryotic cells in culture. When *Pseudomonas* exotoxin A is added to eukaryotic cells, it reduces or prevents protein synthesis in cells, causing cell cytotoxicity. To determine if antisera can reduce or inactivate cell cytotoxicity of *Pseudomonas* exotoxin A, *Pseudomonas* exotoxin A can be incubated with antisera containing antibodies directed against the chimeric protein. This incubated mixture is added to cells in culture. Then, the effect of antisera on the protein synthesis in the cells can be measured (e.g., monitoring the incorporation of [$^3$H] leucine). This assay is described in Example section IVC below and also in Ogata at al., *J. Biol. Chem.* 265(33):20678–85 (1990). If the non-toxic exotoxin A sequence within the chimeric protein is present in near-native conformation, then it is expected that antisera raised against the chimeric protein (at a suitable dilution, e.g., 1:10 or 1:100) can reduce cytotoxicity of *Pseudomonas* exotoxin A by at least about 30%, typically at least about 50%, more typically at least about 70%, 80%, 90%, 95%, or 99% compared to a control (e.g., addition of purified *Pseudomonas* exotoxin A without antisera).

III. Compositions Comprising Chimeric Proteins or Polynucleotides

The invention also provides formulations of one or more chimeric polypeptide or polynucleotide compositions disclosed herein in pharmaceutically-acceptable solutions for administration to a cell or an animal, either alone or in combination with other components.

A. Compositions Comprising Chimeric Proteins

The chimeric protein of the invention can be administered directly to a subject as a pharmaceutical composition. Administration is by any of the routes normally used for introducing a chimeric protein into ultimate contact with the tissue to be treated, preferably the mucosal membrane and epithelial cells. The compositions comprising chimeric proteins are administered in any suitable manner, preferably with pharmaceutically acceptable carriers. Suitable methods of administering such modulators are available and well known to those of skill in the art. Although more than one route can be used to administer a particular composition, a particular route can often provide a more immediate and more effective reaction than another route.

Pharmaceutical compositions comprising the chimeric proteins of the invention may be formulated in conventional manner using one or more physiologically acceptable carriers, diluents, excipients or auxiliaries which facilitate processing of the polypeptides into preparations which can be used pharmaceutically. Proper formulation is dependent upon the route of administration chosen.

Pharmaceutically acceptable carriers, diluents, or excipients are determined in part by the particular composition being administered, as well as by the particular method used to administer the composition. Accordingly, there are a wide variety of suitable formulations of pharmaceutical compositions of the present invention. For example, pharmaceutical compositions can be formulated for topical administration, systemic formulations, injections, transmucosal administration, oral administration, inhalation/nasal administration, rectal or vaginal administrations. Suitable formulations for various administration methods are described in, e.g., *Remington's Pharmaceutical Sciences*, 17th ed. 1985.

Briefly, for topical administration, the proteins may be formulated as solutions, gels, ointments, creams, suspensions, etc. Systemic formulations include those designed for administration by injection, e.g. subcutaneous, intravenous, intramuscular, intrathecal or intraperitoneal injection, as well as those designed for transdermal, transmucosal, oral or pulmonary administration. For injection, the proteins may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. For oral administration, a composition can be readily formulated by combining the chimeric proteins with pharmaceutically acceptable carriers to enable the chimeric proteins to be formulated as tablets, pills, capsules, liquids, gels, syrups, slurries, suspensions and the like. For administration by inhalation, the chimeric proteins for use according to the present invention are conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. The proteins may also be formulated in rectal or vaginal compositions such as suppositories or retention enemas, e.g., containing conventional suppository bases such as cocoa butter or other glycerides.

Other suitable formulations and administration methods will be readily apparent to one of skill in the art and can be applied to the present invention.

B. Compositions Comprising Chimeric Polynucleotides

The invention also provides compositions comprising the polynucleotides encoding the chimeric proteins (sometimes referred to as "chimeric nucleic acids" or "chimeric polynucleotides"). These nucleic acids can be inserted into any of a number of well-known vectors for the transfection of target cells or host tissues. For example, nucleic acids are delivered as DNA plasmids, naked nucleic acid, and nucleic acid complexed with a delivery vehicle such as a liposome. Viral vector delivery systems include DNA and RNA viruses, which have either episomal or integrated genomes after delivery to the cell. For a review of gene therapy procedures, see Anderson, *Science* 256:808–813 (1992); Nabel & Felgner, *TIBTECH* 11:211–217 (1993); Mitani & Caskey, *TIBTECH* 11:162–166 (1993); Dillon, *TIBTECH* 11:167–175 (1993); Miller, *Nature* 357:455–460 (1992); Van Brunt, *Biotechnology* 6(10):1149–1154 (1988); Vigne, *Restorative Neurology and Neuroscience* 8:35–36 (1995); Kremer & Perricaudet, *British Medical Bulletin* 51(1):31–44 (1995); Haddada at al., in *Current Topics in Microbiology and Immunology* Doerfler and Böhm (eds) (1995); and Yu at al., *Gene Therapy* 1:13–26 (1994).

Methods of non-viral delivery of nucleic acids include lipofection, microinjection, biolistics, virosomes, liposomes, immunoliposomes, polycation or lipid:nucleic acid conjugates, naked DNA, artificial virions, and agent-enhanced uptake of DNA. Lipofection is described in, e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424, WO 91/16024. Delivery can be to cells (ex vivo administration) or target tissues (in vivo administration).

C. Vaccines

In some preferred embodiments of the present invention, vaccines are provided. The vaccines will generally comprise one or more pharmaceutical compositions, such as those discussed above, in combination with an immunostimulant. An immunostimulant may be any substance that enhances or potentiates an immune response (antibody and/or cell-mediated) to an exogenous antigen. Examples of immunostimulants include adjuvants, biodegradable microspheres (e.g., polylactic galactide) and liposomes (into which the compound is incorporated; see, e.g., Fullerton, U.S. Pat. No. 4,235,877). Vaccine preparation is generally described in, for example, Powell & Newman, eds., *Vaccine Design* (the subunit and adjuvant approach) (1995). Pharmaceutical compositions and vaccines within the scope of the present invention may also contain other compounds, which may be biologically active or inactive.

Any of a variety of immunostimulants may be employed in the vaccines of this invention. For example, an adjuvant may be included. Most adjuvants contain a substance designed to protect the antigen from rapid catabolism, such as aluminum hydroxide or mineral oil, and a stimulator of immune responses, such as lipid A. Suitable adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); AS-2 and derivatives thereof (SmithKline Beecham, Philadelphia, Pa.); CWS, TDM, Leif, aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF or interleukin-2, -7, or -12, may also be used as adjuvants.

Any suitable carrier known in the art can be employed in the vaccines of the invention, and the type of carrier will vary depending on the mode of administration. The vaccines can be formulated for any appropriate manner of administration, including for example, topical, oral, nasal, intravenous, intracranial, intraperitoneal, subcutaneous or intramuscular administration. These formulations and administration methods are described above, and will not be repeated in this section.

Pharmaceutical compositions and vaccines of the present invention may be presented in unit-dose or multi-dose containers, such as sealed vials. Such containers are preferably hermetically sealed to preserve sterility of the formulation until use. In general, formulations can be stored as suspensions, solutions or emulsions in oily or aqueous vehicles. Alternatively, a pharmaceutical composition or vaccine may be stored in a freeze-dried condition requiring only the addition of a sterile liquid carrier immediately prior to use.

D. Effective Dose

Determination of an effective amount of the chimeric protein for inducing an immune response in a subject is well within the capabilities of those skilled in the art, especially in light of the detailed disclosure provided herein.

An effective dose can be estimated initially from in vitro assays. For example, a dose can be formulated in animal models to achieve an induction of an immune response using techniques that are well known in the art. One having ordinary skill in the art could readily optimize administration to humans based on animal data. Dosage amount and interval may be adjusted individually. For example, when used as a vaccine, the polypeptides and/or polynucleotides of the invention may be administered in about 1 to 3 doses for a 1–36 week period. Preferably, 3 doses are administered, at intervals of about 3–4 months, and booster vaccinations may be given periodically thereafter. Alternate protocols may be appropriate for individual patients. A suitable dose is an amount of polypeptide or DNA that, when administered as described above, is capable of raising an immune response in an immunized patient sufficient to protect the patient from infections by microorganisms expressing Type IV pilin sequence for at least 1–2 years. In general, the amount of polypeptide or nucleic acid present in a dose (or produced in situ by the DNA in a dose) ranges from about 1 pg to about 5 mg per kg host, typically from about 10 pg to about 1 mg, and preferably from about 100 pg to about 1 μg. Suitable dose range will vary with the size of the patient, but will typically range from about 0.1 mL to about 5 mL.

IV. Methods of Eliciting an Immune Response

The chimeric proteins of the invention are useful in eliciting an immune response in a host. Eliciting a humoral immune response is useful in the production of antibodies that specifically recognize the Type IV pilin loop sequence or the non-toxic exotoxin A sequence and in immunization against microorganisms that bear the Type IV pilin sequence.

A. Prophylactic and Therapeutic Treatments

The chimeric proteins can include the Type IV pilin loop sequences from various pathogenic microorganisms, including *Pseudomonas aeruginosa, Neisseria meningitides, Neisseria gonorrhoeae, Vibro cholera*, etc. Accordingly, this invention provides prophylactic and therapeutic treatments for diseases involving the pathological activity of pathogens bearing the Type IV pilin loop sequences. The methods involve immunizing a subject with non-toxic *Pseudomonas* exotoxin A based chimeric proteins bearing the Type IV pilin sequence. The resulting immune responses mount an attack against the pathogens, themselves. For example, if the pathology results from bacterial or yeast infection, the immune system mounts a response against the pathogens.

B. Humoral Immune Response

The chimeric proteins are useful in eliciting the production of antibodies against the Type IV loop pilin sequence and the non-toxic *Pseudomonas* exotoxin A sequence by a subject. The chimeric proteins are attractive immunogens for making antibodies against the Type IV pilin loop sequences that naturally occur within a cysteine-cysteine loop: Because they contain the Type IV pilin loop sequences within a cysteine-cysteine loop, they present the Type IV pilin loop sequence to the immune system in near-native conformation. The resulting antibodies generally recognize the native antigen better than those raised against linearized versions of the Type IV pilin sequence.

Methods for producing polyclonal antibodies are known to those of skill in the art. In brief, an immunogen, preferably a purified polypeptide, a polypeptide coupled to an appropriate carrier (e.g., GST, keyhole limpet hemanocyanin, etc.), or a polypeptide incorporated into an immunization vector, such as a recombinant vaccinia virus (see, U.S. Pat. No. 4,722,848) is mixed with an adjuvant. Animals are immunized with the mixture. An animal's immune response to the immunogenic preparation is monitored by taking test bleeds and determining the titer of reactivity to the polypeptide of interest. When appropriately high titers of antibody to the immunogen are obtained, blood is collected from the animal and antisera are prepared. Further fractionation of the antisera to enrich for antibodies reactive to the polypeptide is performed where desired. See, e.g., Coligan, Current Protocols in Immunology Wiley/Greene, NY (1991); and Harlow and Lane, Antibodies: A Laboratory Manual Cold Spring Harbor Press, NY (1989).

In various embodiments, the antibodies ultimately produced can be monoclonal antibodies, humanized antibodies, chimeric antibodies or antibody fragments.

Monoclonal antibodies are prepared from cells secreting the desired antibody. These antibodies are screened for binding to polypeptides comprising the epitope, or screened for agonistic or antagonistic activity, e.g., activity mediated through the agent comprising the non-native epitope. In some instances, it is desirable to prepare monoclonal antibodies from various mammalian hosts, such as mice, rodents, primates, humans, etc. Description of techniques for preparing such monoclonal antibodies are found in, e.g., Stites et al (eds.) Basic and Clinical Immunology (4th ed.) Lange Medical Publications, Los Altos, Calif., and references cited therein; Harlow and Lane, Supra; Goding (1986) Monoclonal Antibodies: Principles and Practice (2d ed.) Academic Press, New York, N.Y.; and Kohler and Milstein (1975) Nature 256: 495–497.

In another embodiment, the antibodies are humanized immunoglobulins. Humanized antibodies are made by linking the CDR regions of non-human antibodies to human constant regions by recombinant DNA techniques. See Queen et al., U.S. Pat. No. 5,585,089.

In another embodiment of the invention, fragments of antibodies against the Type IV pilin loop sequence are provided. Typically, these fragments exhibit specific binding to the Type IV pilin loop sequence similar to that of a complete immunoglobulin. Antibody fragments include separate heavy chains, light chains, Fab, Fab' F(ab')$_2$ and Fv. Fragments are produced by recombinant DNA techniques, or by enzymatic or chemical separation of intact immunoglobulins.

Other suitable techniques involve selection of libraries of recombinant antibodies in phage or similar vectors. See, Huse et al., Science 246: 1275–1281 (1989); and Ward et al., Nature 341: 544–546 (1989).

An approach for isolating DNA sequences which encode a human monoclonal antibody or a binding fragment thereof is by screening a DNA library from human B cells according to the general protocol outlined by Huse at al., Science 246:1275–1281 (1989) and then cloning and amplifying the sequences which encode the antibody (or binding fragment) of the desired specificity. The protocol described by Huse is rendered more efficient in combination with phage display technology. See, e.g., Dower at al., WO 91/17271 and McCafferty at al., WO 92/01047. Phage display technology can also be used to mutagenize CDR regions of antibodies previously shown to have affinity for the polypeptides of this invention or their ligands. Antibodies having improved binding affinity are selected.

The antibodies of this invention are useful for affinity chromatography in isolating agents bearing the Type IV pilin sequence. Columns are prepared, e.g., with the antibodies linked to a solid support, e.g., particles, such as agarose, Sephadex, or the like, where a cell lysate is passed through the column, washed, and treated with increasing concentrations of a mild denaturant, whereby purified agents are released.

As described in the Example section, sera from immunized rabbits had two reactivities: one that blocks adhesion and one that neutralizes exotoxin A. Therefore, by introducing the chimeric protein as a composition (e.g., a vaccine) into a subject, antibodies that prevent colonization of microorganisms bearing Type IV pilin sequences (e.g., *Pseudomonas aeruginosa*) can be provided in the subject. In particular for *Pseudomonas aeruginosa*, should small numbers of these bacteria overcome this defense, the normal destructive power of the exotoxin A will be also neutralized by the antisera.

C. IgA-mediated Secretory Immune Response

Mucosal membranes are primary entryways for many infectious pathogens, including those bearing the Type IV pilin sequences. Mucosal membranes include, e.g., the mouth, nose, throat, lung, vagina, rectum and colon. As a defense against entry, the body secretes secretory IgA on the surfaces of mucosal epithelial membranes against pathogens. Furthermore, antigens presented at one mucosal surface can trigger responses at other mucosal surfaces due to trafficking of antibody-secreting cells between these mucosae. The structure of secretory IgA has been suggested to be crucial for its sustained residence and effective function at the luminal surface of a mucosa. As used herein, "secretory IgA" or "sIgA" refers to a polymeric molecule comprising two IgA immunoglobulins joined by a J chain and further bound to a secretory component. While mucosal administration of antigens can generate an IgG response, parenteral administration of immunogens rarely produce strong sIgA responses.

*Pseudomonas* exotoxin binds to receptors on mucosal membranes. Therefore, the chimeric proteins comprising non-toxic exotoxin A sequences are an attractive vector for bringing the type IV pilin loop sequence to a mucosal surface. There, the chimeric proteins elicit an IgA-mediated immune response against the chimeric proteins. Accordingly, this invention provides the non-toxic *Pseudomonas* exotoxin A-based chimeric proteins comprising a Type IV pilin loop sequence from a pathogen that gains entry through mucosal membranes. The cell recognition domain can be targeted to any mucosal surface receptor. These chimeric proteins are useful for eliciting an IgA-mediated secretory immune response against immunogens that gain entry to the body through mucosal surfaces. The chimeric proteins used for this purpose should have ligands that bind to receptors on mucosal membranes as their cell recognition domains. For example, epidermal growth factor binds to the epidermal growth factor receptor on mucosal surfaces.

The chimeric proteins can be applied to the mucosal surface by any of the typical means, including pharmaceutical compositions in the form of liquids or solids, e.g., sprays, ointments, suppositories or erodible polymers impregnated with the immunogen. Administration can involve applying the immunogen to a plurality of different mucosal surfaces in a series of immunizations, e.g., as booster immunizations. A booster inoculation can also be administered parenterally, e.g., subcutaneously. The chimeric protein can be administered in doses of about 1 μg to 1000 μg, e.g., about 10 μg to 100 μg.

The IgA response is strongest on mucosal surfaces exposed to the immunogen. Therefore, in one embodiment, the immunogen is applied to a mucosal surface that is likely to be a site of exposure to the particular pathogen. Accordingly, depending on the site of exposure to the particular pathogen, the chimeric proteins can be administered to the lung, nasal mucosa, vaginal, anal or oral mucosal surfaces, or they can be given as an oral medication. For example, for cystic fibrosis patients, the chimeric proteins can be administered to the lung.

Mucosal administration of the chimeric protein of this invention result in strong memory responses, both for IgA and IgG. Therefore, in vaccination with them, it is useful to provide booster doses either mucosally or parenterally. The memory response can be elicited by administering a booster dose more than a year after the initial dose. For example, a booster dose can be administered about 12, about 16, about 20 or about 24 months after the initial dose.

The potential value of a *Pseudomonas* vaccine relates in part to its ability to protect individuals broadly from the strains that are present in the environment. Based on the length of the pilin loop insert, there are two groupings for *Ps. aeruginosa*: one group with a 12 amino acid sequence and one with a 17 amino acid insert. Both loops apparently bind asialo-GM1 and are thought to exhibit similar structures. Reflecting this, we note that our vaccine protein, containing a 12 amino acid loop from the PAK strain, was able to generate antibodies that were reactive not only for strains with the shorter loop but also for the SBI-N strain, which displayed the longer loop. Our studies have also provided additional sequence data for pilin and pilin loop sequences. We report here two pilin loop sequences (those for *Ps. aeruginosa* strain 1071 and *Ps. aeruginosa* strain SBI-N) that have not previously been entered in databases (Tables 1 and 2).

Chronic pulmonary colonization by *Ps. aeruginosa* is associated with a decline in the clinical course of CF patients. Frequently, antibiotic therapy, even via pulmonary delivery, fails to eradicate *Ps. aeruginosa* infections in these patients (Steinkamp, G., B. et al. *Pediatr Pulmonol* 6(2): 91–8(1989)). Controlling *Ps. aeruginosa* infections, or better yet, preventing them, has thus become a critical unmet medical need in the care of CF patients ((Bauernfeind, A. et al. *Behring Inst Mitt*(98):256–61 (1997)). To address this, a number of vaccine approaches have been explored, many focused on outer membrane constituents (Matthews-Greer, J. M., et al.; *J Infect Dis* 155(6): 1282–91 (1987); Owen, P. Biochem Soc Trans 20(1):1–6 (1992); Sawa, et al.; *Nat Med* 5(4):392–8(1999), some on toxins (Chen, T. Y., et al. *J Biomed Sci* 6(5):357–63 (1999); Denis-Mize, K. S., et al.; *FEMS Immunol Med Microbiol* 27(2):147–54 (2000); Gilleland, H. E., et al.; *J Med Microbiol* 38(2):79–86 (1993); Matsumoto, et al.; *J Med Microbiol* 47(4):303–8 (1988)), and some on a combination approach (Cryz, S. J., et al.; *Antibiot Chemother* 39:249–55 (1987); Cryz, S. J., et al. *Infect Immun* 52(1):161–5 (1986); Cryz, S. J., et al.; *Infect Immun* 55(7):1547–51 (1987); and Cryz, S. J., et al. *J Infect Dis* 154(4):682–8 (1986) (Johansen, H. K., et al.; *APMIS* 102(7):545–53(1994).

The compositions of the present invention in some embodiments are used to treat persons at risk of infection and particularly, *Pseudomonas aeruginosa* infection. These persons include, in particular, hospitalized patients having cystic fibrosis, bum wounds, organ transplants, compromised immune function, or intravenous-drug addition.

Previously, we compared the subcutaneous route with mucosal delivery of toxin-V3 loop proteins (Mrsny, R. at al., *Vaccine* 17(11–12):1425–33 (1999). Results of mucosal vaccination indicated that a robust anti-V3 loop response could be achieved with high titer responses of both serum IgG and secretory IgA antibodies. Because the toxin-pilin chimeric protein is a candidate vaccine to prevent *Pseudomonas* colonization in CF, one embodiment provides a vaccine delivered to target mucosal antibody responses at airway epithelia.

EXAMPLES

I. Construction of Plasmids

Figure 3:
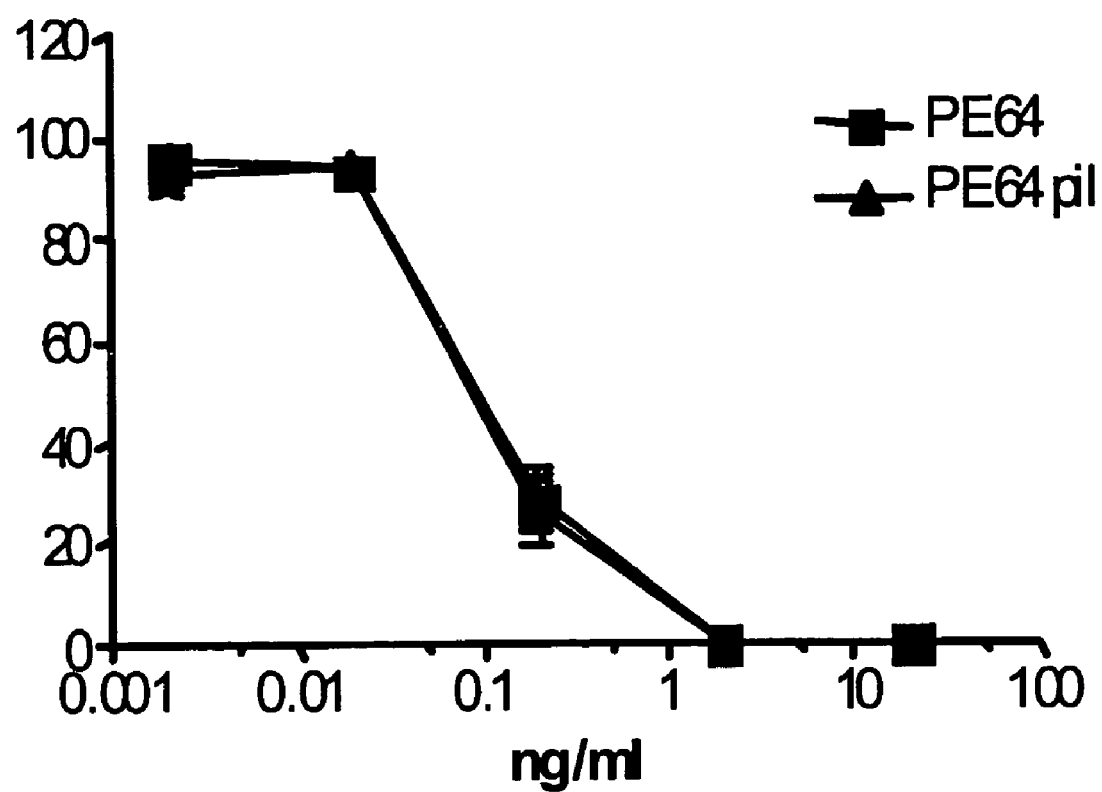
FIG. 3 illustrates the toxicity of PE64pil compared to PE64. To assess the effect of introducing a third party loop into PE, we compared the toxicity of PE64 (■) with PE64pil (▲). Increasing concentrations of each protein was added to L929 cells and, after an overnight incubation, inhibition of protein synthesis was determined. Results are expressed as percent control compared to cells receiving no toxin. Error bars represent one SD of the mean from triplicate wells.

Four plasmids, pPE64, pPE64Δ553, pPE64pil, pPE64Δ553pil, were constructed. Plasmid pPE64 encodes native the *Pseudomonas* exotoxin A, except the plasmid encoded a slightly smaller version of PE that lacked much of domain Ib and has a novel PstI site in domain Ib as described in detail below. Plasmid pPE64Δ553 encodes the a non-toxic version of plasmid pPE64, whereby the plasmid pPE64 was modified by subcloning to introduce the enzymatically inactive domain III of PE (i.e., Glu at amino acid position 553 is deleted). To generate a PE-based pilin chimeric protein, an oligonucleotide duplex that encoded amino acids 129–142 from the PAK strain of pilin was synthesized. Then plasmid pPE64pil is constructed based on plasmid pPE64, wherein a pilin loop sequence from *P. aeruginosa* PAK strain was inserted into the PstI site of plasmid pPE64. Plasmid pPE64Δ553pil is constructed based on plasmid pPE64Δ553, wherein a pilin loop sequence from *P. aeruginosa* PAK strain was inserted into the PstI site of plasmid pPE64Δ553. All of these vectors were constructed without a bacterial secretion sequence which allowed recombinant proteins to be expressed as inclusion bodies.

Specifically, plasmids pPE64 and pPE64Δ553 are constructed as follows. Plasmid pMOA1A2VK352 (Ogata et al., *J. Biol. Chem.* 267, 25396–401 (1992)), encoding PE, was digested with Sfi1 and ApaI (residues 1143 and 1275, respectively) and then re-ligated with a duplex containing a novel Pst1 site. The coding strand of the duplex had the following sequence: 5'-tggccctgac cctggccgcc gccgagagcg agcgcttcgt ccggcagggc accggcaacg acgaggccgg cgcggcaaac ctgcagggcc-3' (SEQ ID NO:31). The resulting plasmid encoded a slightly smaller version of PB and lacked much of domain Ib. The Pst1 site was then used to introduce duplexes encoding pilin loop sequences flanked by cysteine residues. To make non-toxic proteins, vectors were modified by the subcloning in an enzymatically inactive domain III from pVC45ΔE553. An additional subcloning, from pJH4 (Hwang et. al., *Cell* 48:129–136 (1987)), was needed to produce a vector that lacked a signal sequence. Construction of plasmids pPE64 and pPE64Δ553 are also described in FitzGerald et al., *J. Biol. Chem.* 273(16):9951–8 (1998).

Plasmids pPE64pil and pPE64Δ553pil with a pilin loop sequence insert were constructed based on plasmids pPE64 and pPE64Δ553, respectively. A 54 bp sense oligonucleotide with cohesive ends for PstI and encoding the 12 amino acid pilin loop of the PAK strain, was annealed with a 54 bp antisense oligonucleotide in 10 mM Tris/HCl, 50 mM NaCl pH 7.4. The sense and antisense oligonucleotides had the following sequences:

```
Sense
                                    (SEQ ID NO:32)
5'-TTGTACTAGTGATCAGGATGAACAGTTTATTCCGAAAGGTTGTTCAC

GTATGCA-3';

Antisense
                                    (SEQ ID NO:33)
5'-TACGTGAACAACCTTTCGGAATAAACTGTTCATCCTGATCACTAGTA

CAATGCA-3'.
```

Annealing was accomplished by heating to 94° C. for 5 mm followed by cooling to 25° C. over a period of 40 mm Plasmids pPE64 and pPE64Δ5532), encoding enzymatically active and inactive PE respectively, were digested with PstI at residue 1470. (FitzGerald, D. J., et al., *J Biol Chem* 273(16):9951–8 (1998). Ligation with the phosphorylated pilin oligoduplex destroyed the PstI site and introduced a unique SpeI site. A XhoI/SpeI double digest was used to check for the correct orientation of the insert. Ligation of the pilin oligoduplex into the PstI-cut vector was followed by several characterization steps to confirm the presence of the pilin insert in the correct orientation. Final constructs were verified by dideoxy double strand sequencing.

II. Expression and Characterization of Proteins

A. Expression and Purification

Using the T7 expression system described by Studier at al., (*Methods Enzymol*. 185:60–89 (1990)), four PE-related proteins were expressed *E. coli*. These included PE64, PE64Δ553, PE64pil and PE64Δ553pil.

Chimeric proteins were expressed and isolated as inclusion bodies as described in Buchner et al., *Anal. Biochem.* 205(2):263–70 (1992). Each protein was expressed separately and purified to near homogeneity. Briefly, strain BL21(λDE3) was transformed with plasmids harboring a T7 promoter upstream of the initial ATG of the toxin-expressing vectors. Cultures were grown in Superbroth (KD Medical, Bethesda, Md.) with ampicillin (50 ug/ml) and then induced for protein expression by the addition of IPTG (1 mM). After two hours of further culture, bacterial cells were harvested by centrifugation. Following cell lysis, expressed proteins were recovered in inclusion bodies.

Proteins were solubilized with Guanidine HCl (6.0 M), 2 mM EDTA pH 8.0 plus dithioerythreitol (65 mM). Solubilized proteins were then refolded by dilution into a redox shuffling buffer (Buchner et al., *Anal. Biochem.* 205(2): 263–70 (1992). Refolded proteins were dialyzed against a 20 mM Tris, 100 mM urea pH 7.4, adsorbed on Q Sepharose (Amersham Pharmacia Biotech), washed with 150 mM NaCl, 20 mM Tris, 1 mM EDTA pH 6.5 and eluted with 280 mM NaCl, 20 mM Tris, 1 mM EDTA. Eluted proteins were diluted 5-fold and then adsorbed onto a MonoQ column (HR 10/10, Amersham Pharmacia Biotech) and further purified by the application of a linear salt gradient (0–0.4 M NaCl in Tris EDTA, pH 7.4). PE proteins eluted between 0.2 and 0.25 M NaCl. Final purification was achieved using a gel filtration column (Superdex 200, Amersham Pharmacia Biotech) in PBS, pH 7.4.

B. Characterization of Proteins

1. Western Blot Analysis

The PK99H mouse monoclonal antibody and purified pilin proteins were obtained from Dr. Randall Irvin, University of Alberta, Canada. Antimouse IgG and antirabbit IgG antibodies were used to detect primary antibodies in Western blots and ELISAs (available from Jackson Immuno Research Lab, West Grove, Pa.).

Proteins were initially analyzed by SDS-PAGE (FIG. 2A). Substantially pure proteins were obtained using the purification scheme outlined above. In Western blot analysis the PE64pil and PE64Δ553pil proteins reacted with PK99H, a monoclonal antibody to the C-terminal loop of pilin (FIG. 2B). The same antibody also reacted with soluble preparations of the same proteins, indicating that the pilin insert was exposed on the surface of the PE-pilin chimeric protein. PE proteins without inserts did not react with the PK99H antibody (FIG. 2B).

2. Cytotoxicity Assay

To investigate the influence of the pilin insert on toxin structure and function, the two enzymatically active proteins, PE64 and PE64pil, were compared in a cytotoxicity assay. Cytotoxicity assay methods described in Ogata et al., *J. Biol. Chem.* 265(33):20678–85 (1990) was used. Concentrations of PE64 or PE64pil ranging from 0.002–20 ng/ml were added to L929 cells for an overnight incubation. Cytotoxicity was then determined by measuring the inhibition of cellular protein synthesis (e.g., monitoring the incorporation of $^3$H-leucine). Data indicated that PE64 and PE64pil exhibited similar toxicities with $IC_{50}$ values in the range of 0.1 ng/ml for both proteins (FIG. 3). This result suggested that the insert of 14 amino acids did not unduly perturb toxin function and, by inference, toxin structure.

3. Reactivity with Immobilized Asialo-GM1

Previous results had indicated that synthetic peptides derived from the C-terminus of pilin could block the binding of pili to epithelial cells (Irvin at al., *Infect. Immun.* 57(12): 3720–6 (1989); Yu, L. at al., *Mol Microbiol* 19(5):1107–16 (1996)). Blocking was attributed to peptide binding to asialo-GM1 on the surface of epithelial cells. To test the functionality of the pilin insert in the PE64 proteins, various concentrations of PE64pil were assayed for reactivity with immobilized asialo-GM1.

96-well plates were coated with asialo-GM1 or monosialo-GM1 (Sigma Chem Co, St Louis, Mo.) that had been solubilized in methanol. A 100 µl solution of ganglioside (5 µg/ml) was added to each well and evaporated at 4° C. until dry. Wells were washed 3 times with PBS and blocked with Fish-gelatin-PBS (BioFX, Randallstown, USA) for 16 h at 4° C. Test proteins in blocking buffer were added at various concentrations. After incubation for 1 h at 22° C., the supernatant was removed and bound protein was detected using heat-inactivated anti PE64Δ553pil serum (1:100) as the primary antibody. For competition studies, proteins at 0.2 ug/ml were incubated with 2 ug/ml of asialo-GM1 or monosialo-GM1 for 30 min at room temperature. Samples were then added to asialo-GM1 coated plates as above.

Figure 4A:
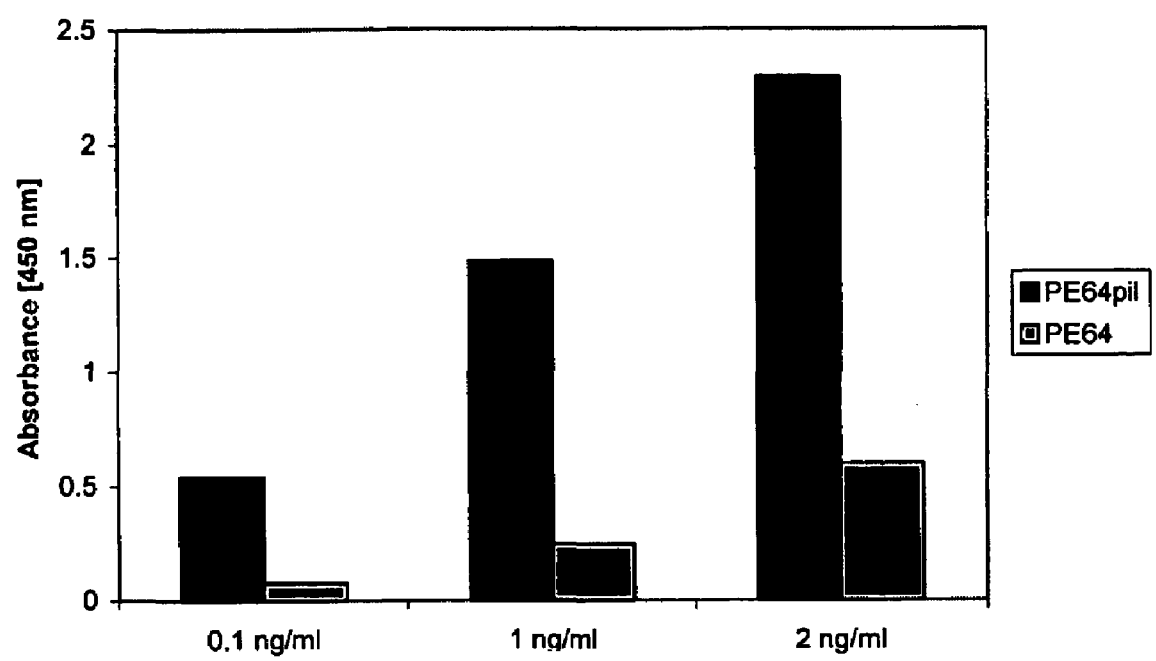
FIGS. 4A, 4B and 4C illustrate the interaction of PE64pil and PE64Δ553pil with immobilized asialo-GM1. (A). Various concentrations of PE64pil or PE64 were added to plates coated with asialo-GM1 and binding was determined by reactivity with rabbit anti-PE followed by a peroxidase labeled goat anti-rabbit IgG antibody. Absorbance at 450 nm was used to monitor binding. (B). and (C). To investigate ganglioside specificity, a competition assay was devised whereby soluble asialo-GM1 or monosialo-GM1 at 2 ug/ml was preincubated with PE64pil (B) or PE64Δ553pil (C) and the percent residual binding determined as described in panel (A). For (B) and (C), graphs show the mean of a representative triplicate experiment. Error bars represent one SD. N.A.=no addition of competitor.
Figure 4B:
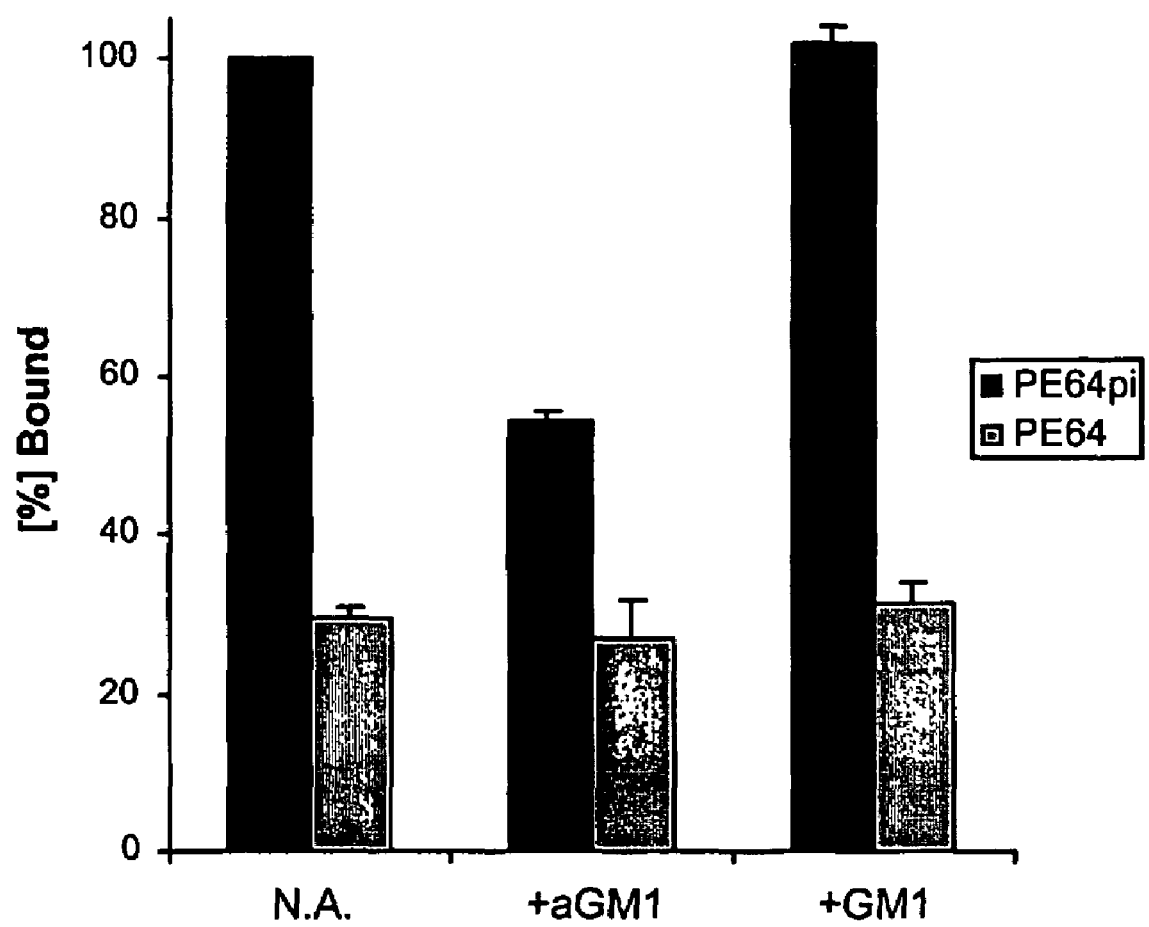
Figure 4C:
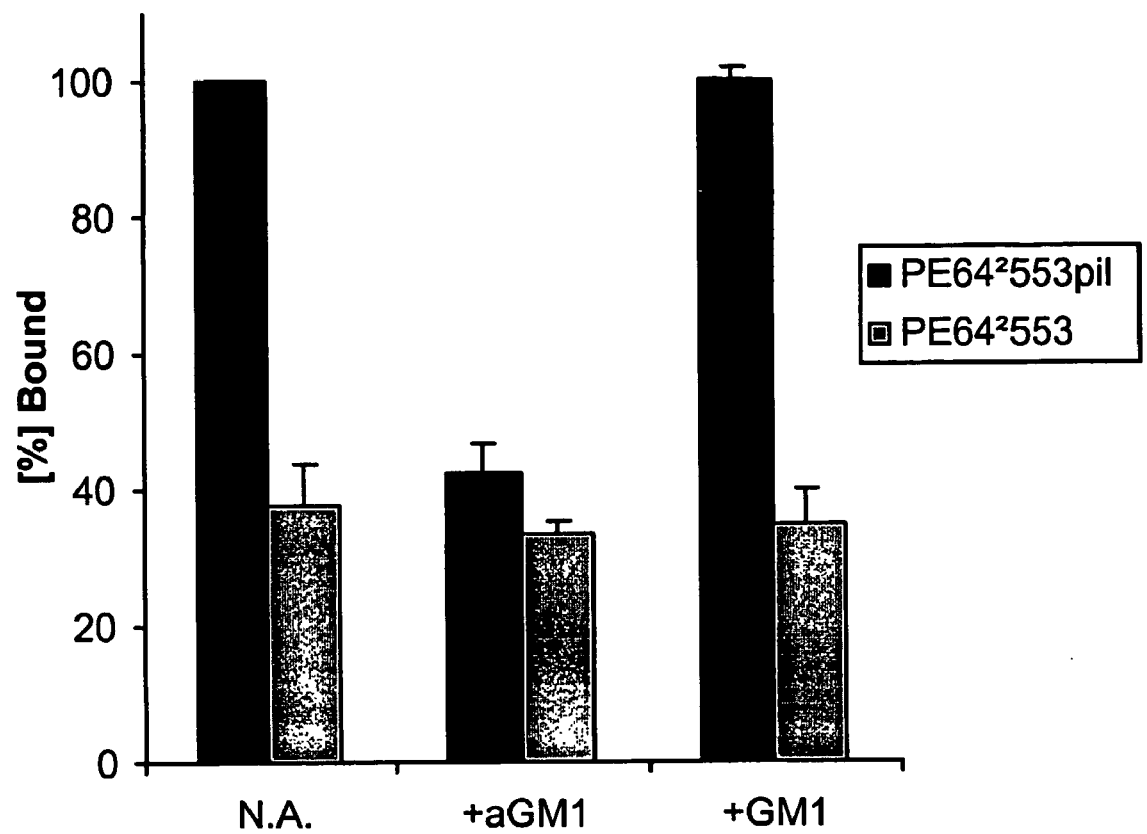

Increasing concentrations of PE64pil from 0.1–2.0 ug/ml reacted specifically with immobilized asialo-GM1 (FIG. 4A). PE64 was used as a control and exhibited only a low level of binding (FIG. 4A). Additional studies were carried out to confirm the ganglioside specificity of both PE64pil and PE64Δ553pil. Soluble asialo-GM1 reduced the binding of PE64pil and PE64Δ553pil to immobilized asialo-GM1 while the addition of monosialo-GM1 did not (FIGS. 4B and 4C). Neither ganglioside interfered with the low level binding of PE64 and PE64Δ553 (FIGS. 4B and 4C). Taken together, these results confirmed not only the presence of reactive pilin sequences but revealed a gain-of-function for the PE64pil proteins.

III. Adhesion Assays

A. *Pseudomonas* Strains

The following strains of *Pseudomonas* were used in adhesion and other assays: PAK, PAO1, SBN-1, 1071, M2, 82932, 82935 and 90063. *Pseudomonas* strains used for adherence studies were grown on LB agar and then in M9 minimal medium (KD Medical, Bethesda, Md.) supplemented with 0.4% glucose at 30° C. without shaking. Cultures in late log phase were routinely used for adhesion assays.

B. Cell Cultures

A549 (ATCC, CCL-185), L929 (ATCC, CCL-1), WI 38, Vero and CHO cells were maintained in DMEM/F12 or RMPI 1640 supplemented with 10% fetal bovine serum (FBS), 2.5 mM glutamine, standard Penicillin/Streptomycin (100 U/100 ug/ml, GibcoBRL, Grand Island, USA) (further designed as complete medium) in 5% $CO_2$ at 37° C. Cells were fed every 2 to 3 days and passaged every 5 to 7 days. For assays, cells were seeded into 24-well or 96-well plates and grown to confluence.

C. Quantification of Bacterial Adherence

To quantify the association of *Pseudomonas* with A549 cells, we followed the adhesion assay described by Chi et al., *Infect. Immun.* 59(3):822–8 (1991). Briefly, A549 cells were grown in a 24 well plates (antibiotic free medium), to a density of approximately $2 \times 10^4$ cells per well. Cells were washed three times in HBSS without serum and were overlayed with 0.5 ml of DMEM/F12 complete medium without FBS. A MOI of 20 was achieved by adding 10 µl of an appropriate bacterial dilution. Plates were incubated for 1 or 2 h at 37° C., 5% $CO_2$.

To remove unbound bacteria, cells were gently washed three times with HBSS. Cells were then fixed for 1 h in 3.7% paraformaldehyde, 200 mM HEPES, pH 7.2. Cells were washed twice with saline and stained with 10% Giemsa for 10 min. Samples were washed three times with water and examined under light microscopy at 400× magnification. Adherent bacteria were quantified by counting the cell-associated bacteria of one hundred A549 cells.

D. Results

Pilin-mediated adhesion to epithelial cells allows *P. aeruginosa* to initiate an infection. Agents that block adherence will therefore reduce the bacterial burden. The following three peptides were synthesized: a long C-terminal peptide (peptide 1: acetyl-KCTSDQDEQFLPKGCSK-$NH_2$; SEQ ID NO:34) corresponding to amino acids 128–142 of the PAK strain (this peptide was oxidized to allow the formation of a disulfide bond), a core peptide (peptide 2: acetyl-DEQFIPK-$NH_2$; SEQ ID NO:35) corresponding to amino acids 134–140 and a scrambled peptide (peptide 3: acetyl-QIDPEFK-$NH_2$; SEQ ID NO:36) having the same amino acid composition as the core but in a jumbled sequence. To enhance stability, the N-termini of these synthetic peptides were acetylated while the C-termini were amidated. These peptides were custom synthesized by Sigma Genosys. The same peptides were also synthesized with a biotin label.

To test these peptides functionally, an adhesion assay was devised whereby washed bacteria of *P. aeruginosa* PAK strain were added to the human lung epithelial cell line, A549. Specifically, cultures of confluent A549 cells were incubated 60 min at 37° C. with 40 µM peptide 1, 40 µM peptide 2, 40 µM peptide 3, 2 nmol/ml PAK-pilin protein, 2 nmol/ml PE64, 2 nmol/ml PE64Δ553, 2 nmol/ml PE64pil, 2 nmol/ml PE64Δ553pil and 4 nmol/ml bovine albumin. Washed once with prewarmed DMEM and *P. aeruginosa* PAK strain was added at a MOI of approximately 50 in DMEM, 2% FBS. Bacteria were centrifuged onto the cells (700 g, 5 min) and incubated 60 min, 37° C. 5% $CO_2$. Adherence was determined as described above.

Figure 5:
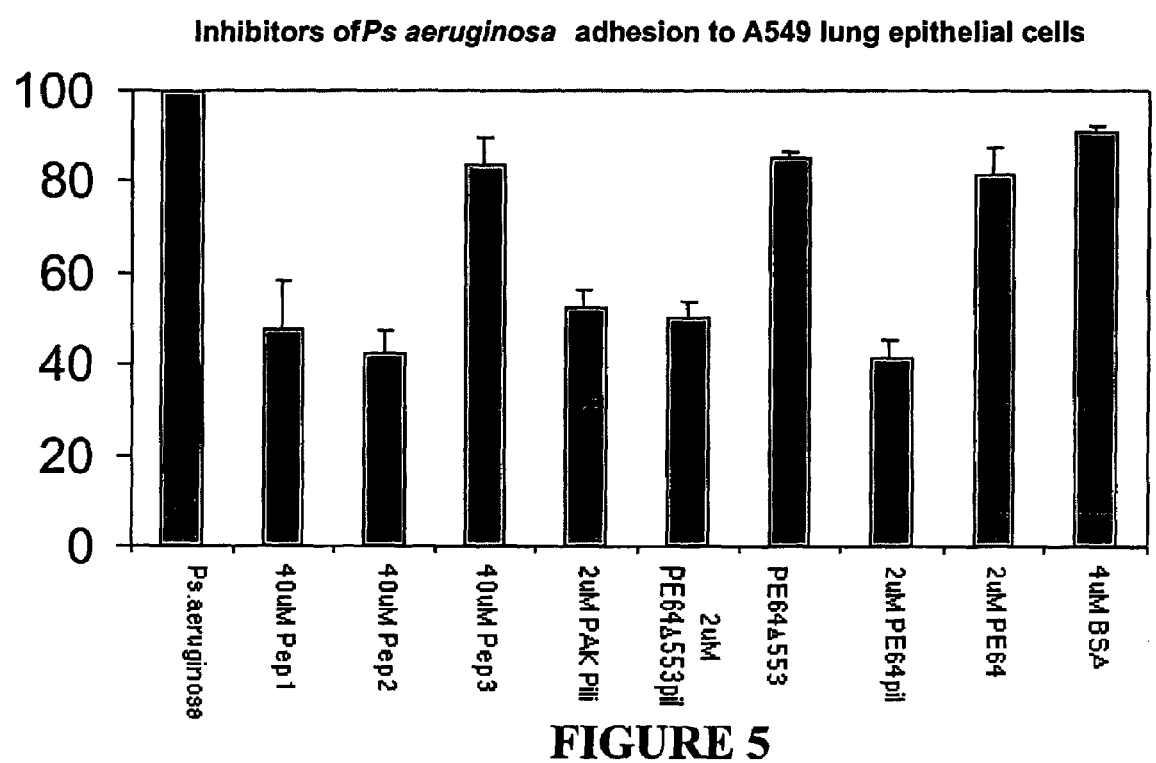
FIG. 5 illustrates adhesion of *Ps. aeruginosa* (PAK strain) to A549 cells. Bacteria were added to cells at an MOI of 100 in the presence or absence of potential inhibitors. Peptides were added to a final concentration of 40 μM, while proteins were added to a concentration of 2 μM. The graph indicates the percentage of cell-bound bacteria compared to samples with no inhibitor. Error bars represent one standard deviation from the mean of three independent experiments.

The results were as follows. Adherence to A549 cells was reduced by approximately 50% in the presence of 40 µM of the long or the core pilin peptide (see FIG. 5). The scrambled peptide did not interfere with adherence.

Because the PE-pilin proteins had exhibited binding activity to asialo-GM1, these were also tested. At approximately the same molar concentration as the synthetic peptides, PE64pil and PE64Δ553pil also blocked bacterial adherence. Effects were due to the presence of the insert, because toxin molecules without insert failed to compete for adherence.

IV. Immune Response to PE64Δ553Pil

A. Production of Polyclonal Antibodies

Figure 6:
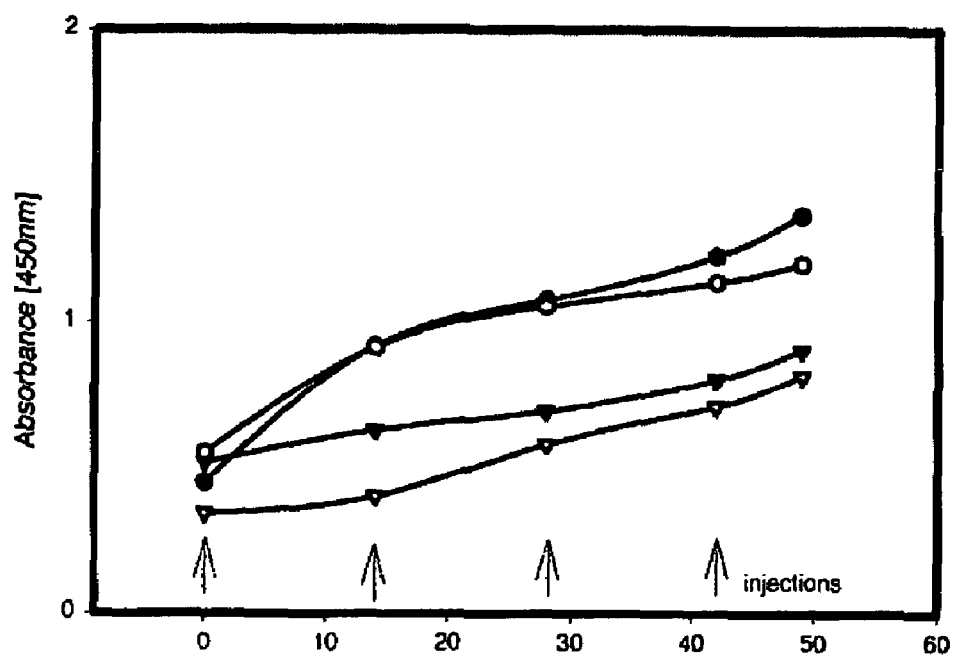
FIG. 6 illustrates antibody titers post immunization with PE64pil with and without adjuvant. Sera were collected from each of four rabbits (numbered 87–90) at various times, diluted 1:100 and then added to streptavidin-coated plates that had been loaded with biotinylated pilin peptides. Rabbit IgG was detected by the addition of a peroxidase conjugated goat anti-rabbit antibody. Rabbits 87 and 88 received adjuvant while rabbits 89 and 90 did not.

To test the ability of the toxin-pilin protein to generate relevant antibody responses, four rabbits were injected with the PE64Δ553pil protein. Two rabbits (numbered 87 and 88) received the protein plus adjuvant (complete Freunds for the first injection followed by incomplete Freunds for subsequent injections) and two (numbered 89 and 90) received the protein alone. Two hundred micrograms of protein per injection was given subcutaneously for a total of four cycles spaced approximately 2 weeks apart. About 12 ml serum was isolated biweekly from each rabbit. The sera were heat inactivated to 20 min, 56° C. and dilutions thereof were used for assays without further purification. Anti-pilin titers were determined using an ELISA assay where biotinylated pilin peptides were immobilized on streptavidin coated plates. Over the period of immunization, anti-pilin titers increased in all four animals (FIG. 6). However, the speed and extent of the response were greater in the two rabbits that received antigen plus adjuvant. To avoid complement-mediated bacterial killing, immune sera were heat inactivated. This treatment did not significantly alter antibody titers in the ELISA assay (data not shown).

B. Inhibition of Adhesion by Post Immunization Sera

To assess antibody mediated inhibition of adherence, anti-PE64Δ553pil rabbit sera were incubated at dilutions from 1:20 to 1:100 with 4×10$^5$ bacteria at 22° C. for 30 min. Bacteria were then centrifuged, resuspended in DMEM without supplements and added to confluent monolayers of A549 cells at a MOI of 20 for 1–2 hrs. Adherence was determined as described above. Immune sera taken after the fourth injection were compared to prebleed samples taken from the same rabbits.

1. Inhibition of *P. aeruginosa* (PAK Strain)

Figure 7A:
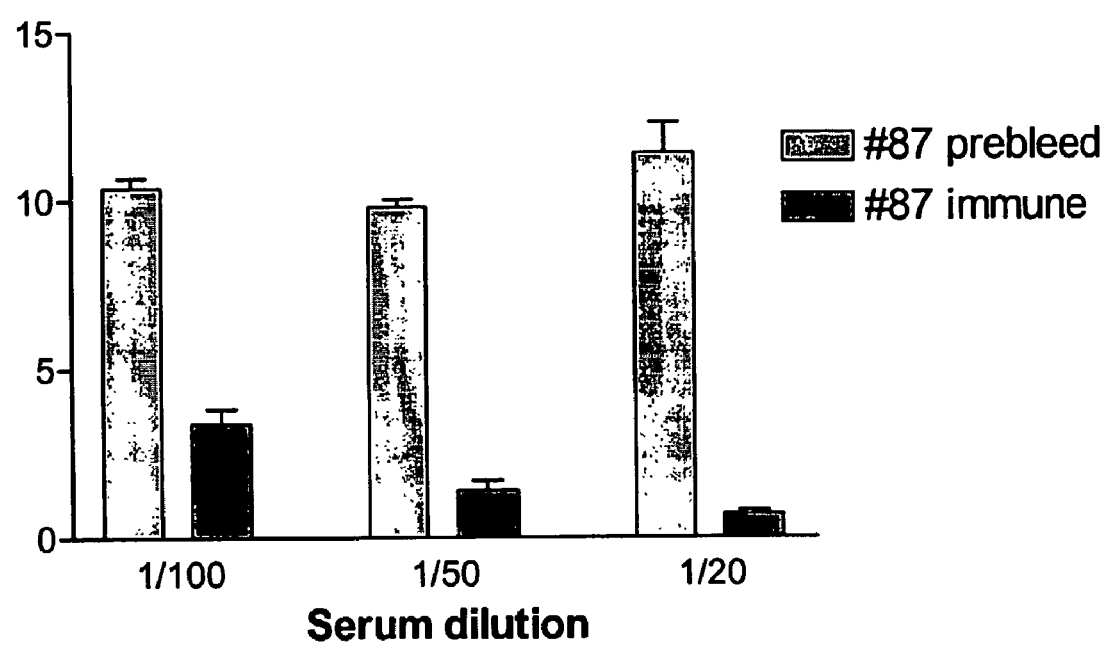
FIGS. 7A, 7B and 7C illustrate antibody-mediated interference with adhesion to A549 cells. (A). The PAK strain of *Ps. aeruginosa* was incubated with 1:20 to 1:100 dilutions of prebleed or immune (taken after the fourth injection of antigen) sera from rabbit #87. Bacteria were then added to cells and the percent adhesion determined by comparison with bacteria that had been incubated in media alone. (B). A 1:20 dilution of sera from each rabbit, prebleed and immune, was tested for antibody mediated interference. (C). Various strains of *Ps. aeruginosa* were incubated with immune sera (1:20) from one of the rabbits that received antigen alone (rabbit #90) and one that received antigen plus adjuvant (rabbit #88). For each panel of FIG. 7, the bar represents the number of bacteria per cell determined by examining one hundred A549 cells. The error bars represent one standard deviation from the mean of three independent experiments.
Figure 7B:
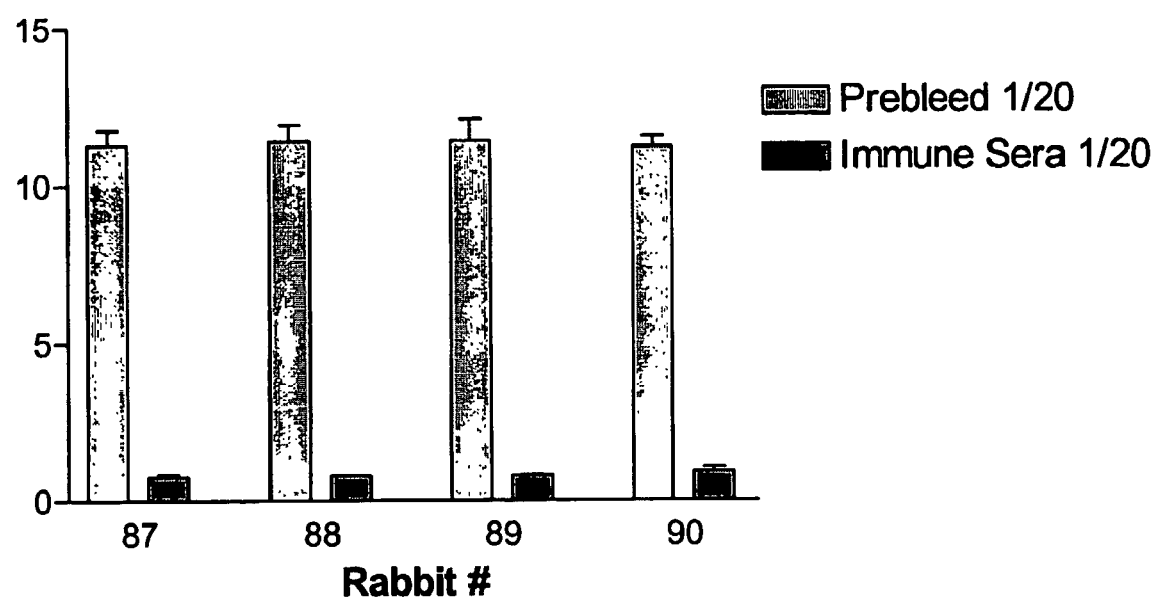

Sera taken 2 weeks after the last injection were assayed for blocking activity in the bacterial adherence assay. Compared to prebleeds, immune sera at various dilutions blocked adherence of the PAK strain of *Ps. aeruginosa* (FIG. 7A). Reduction of adherence ranged from 60% at a dilution of 1:100 to 90% at a dilution of 1:20. At a dilution of 1:20, blocking activity was comparable without regard to the presence of adjuvant in the antigen preparation (FIG. 7B).

2. Inhibition of *P. aeruginosa* (Various Strains)

Figure 7C:
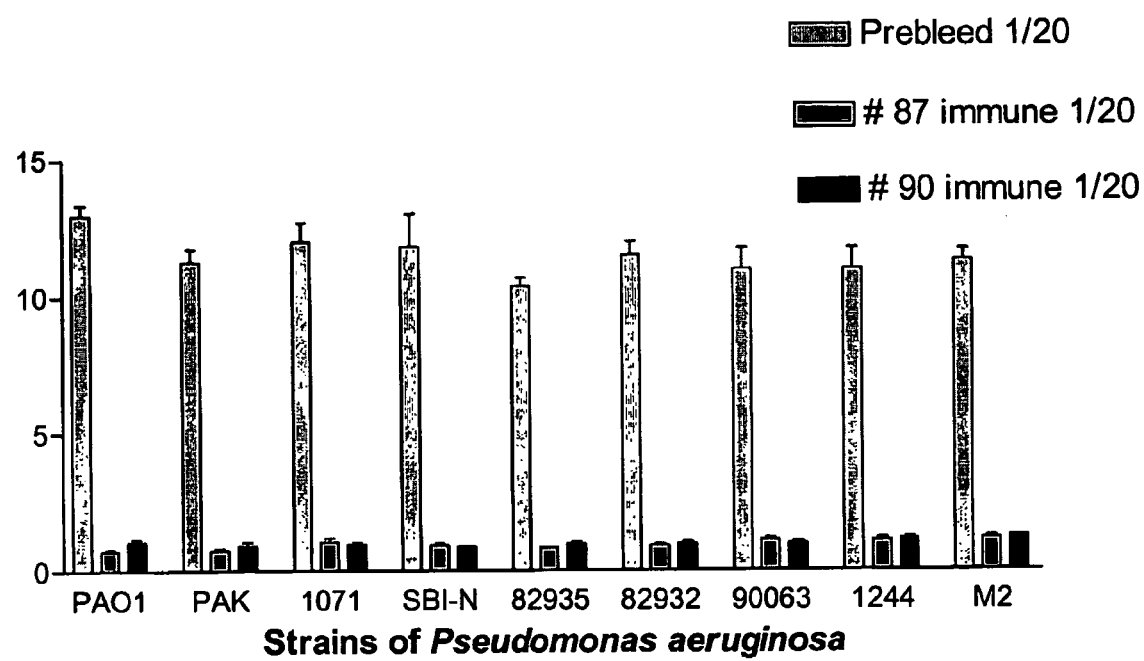

Inhibition of PAK strain adhesion confirmed that rabbits responded to the specific pilin sequence that was administered in the vaccine. However, because the C-terminal loop of pilin exhibits considerable sequence variation, it was important to determine the reactivity of the immune sera for other strains of *Ps. aeruginosa*. Strains PAO1, 1071, SBI-N, 82935, 82932, 90063 1244 and M2 were tested for adherence to A549 cells under similar conditions as the PAK strain. The specific cell binding of all strains were reduced in adhesion when heat inactivated immune rabbit sera were mixed with bacteria at a 1:20 dilution (FIG. 7C). The reduction in adhesion among the different strains was more or less in the range of the PAK strain (about 90% reduction).

While it was unlikely that each of the above strains expressed the same loop sequence as the PAK strain, it was of interest to analyze variations at this portion of the pilin gene. Pilin sequences were determined by generating PCR clones of each strain's pilin gene and sequencing these. Primers for amplification were from the 5' end of the pilin gene and the 3' end of the neighboring gene (Nicotinate-nucleotide pyrophosphorylase) in the *Pseudomonas* genome (to be described in greater detail elsewhere). Results revealed the following: most strains exhibited a 12 amino acid loop while one, SBI-N, had a 17 amino acid loop. Strains 82932 and 82935 had the same loop sequence as KB7 (accession No, Q53391) and 90063 had a loop that matched PAO1 (accession No, A25023). Strains 1071 and SBI-N exhibited loops with novel sequences (See Tables 1 and 2). Strain M2, a mouse isolate, was not sequenced.

B. Toxin Neutralizing Response

The inhibition of protein synthesis of purified PE64 and PE64pil on eukaryotic cells in culture was determined as described in Ogata et al., J. Biol. Chem. 265(33):20678–85 (1990). For inactivating cytotoxic activity, the PE64pil proteins were incubated 30 min at 22° C. with rabbit sera, containing anti PE64Δ553pil antibodies, prior they were added to L929 or A549 cells in 24 well tissue culture dishes.

Figure 8:
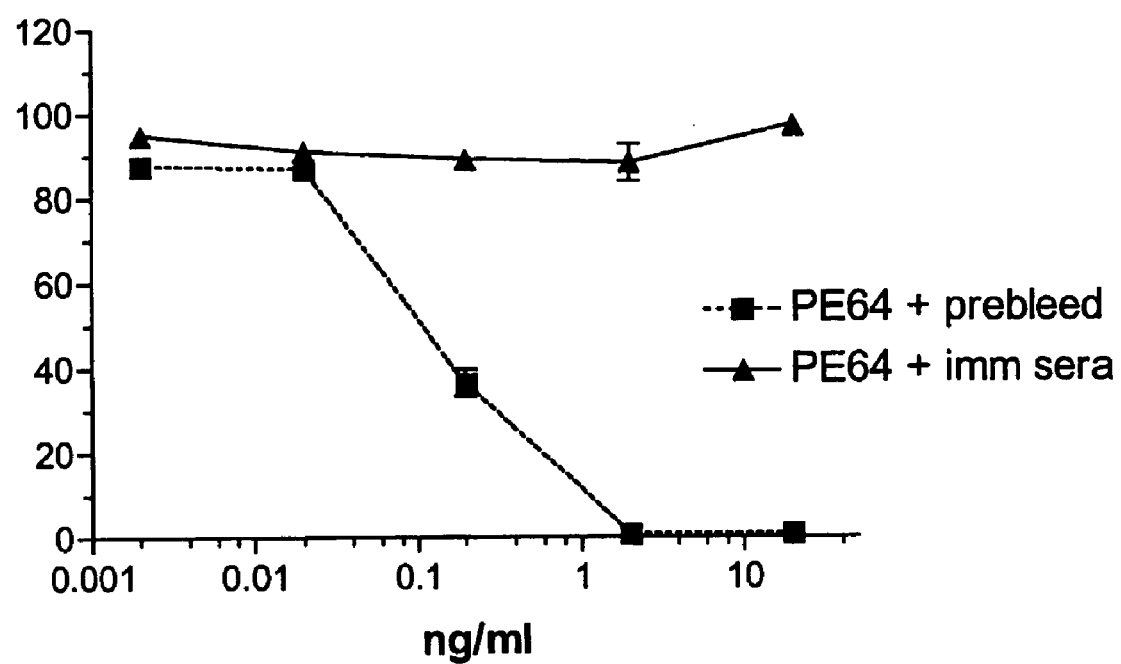
FIG. 8 illustrates antibody-mediated neutralization of PE toxicity. Immune sera (▲) or prebleed sera (■) were diluted 1:20 and mixed with PE64 at 1.0 ug/ml. Samples were then diluted to the concentration indicated and added to L929 cells for an overnight incubation. Results are expressed as percent control of protein synthesis compared to cells receiving no toxin. Error bars represent one SD of the mean from triplicate wells.

Rabbit antisera were evaluated for toxin neutralizing activity. All four of the immunized rabbits at a 1:20 dilution of sera neutralized 1.0 μg/ml of toxin completely (FIG. 8). From these results, it was concluded that PE-pilin vaccine can generate antibodies of two reactivities: one that blocks adhesion and one that neutralizes the exotoxin.

The present invention provides novel materials and methods for chimeric proteins comprising a non-toxic *Pseudomonas* exotoxin A and a Type IV pilin loop sequence. While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined not with reference to the above description, but instead should be determined with reference to the appended claims along with their full scope of equivalents.

All publications and patent documents cited in this application are incorporated by reference in their entirety for all purposes to the same extent as if each individual publication or patent document were so individually denoted. By their citation of various references in this document, Applicants do not admit any particular reference is "prior art" to their invention.

What is claimed is:

1. A chimeric protein comprising: a non-toxic *Pseudomonas* exotoxin A (PE) sequence and a Type IV pilin loop sequence, the Type IV pilin loop sequence being located within the PE sequences wherein the chimeric protein lacks ADP ribosylation activity and comprises: (a) the PE translocation domain or a portion of the PE translocation domain sufficient to effect translocation of the chimeric protein to a cell cytosol; and (b) a portion of the endoplasmic reticulum retention domain sufficient to translocate the chimeric protein from endosome to endoplasmic reticulum; and wherein the pilin loop sequence is located between the portion of the PE translocation domain and the portion of the PE endoplasmic reticulum retention domain; and wherein the Tppe IV pilin loop sequence is selected from the group consisting of SEQ ID NO:3, SEQ ID NO 4, SEQ ID NO:5, SEQ ID NO:6, SEQ ID NO:7, SEQ ID NO:8, SEQ ID NO:9, and SEQ ID NO:10.

2. The chimeric protein of claim 1, wherein the portion of the translocation domain comprises amino acids 280 to 364 of SEQ ID NO:2.

3. The chimeric protein of claim 1, wherein the amino acid sequence of the PE translocation domain consists of the amino acid sequence of positions 253–364 of SEQ ID NO:2 and the endoplasmic reticulum retention domain comprises the amino acid sequence of SEQ ID NO:21, SEQ ID NO:22, or SEQ ID NO:23.

4. A composition comprising a chimeric protein of claim 1 and a pharmaceutically acceptable carrier.

5. A chimeric protein comprising:
a non-toxic Pseudomonas exotoxin A (PE) sequence and a Type IV pilin loop sequence, the Type IV pilin loop sequence being located within the PE sequence, wherein the chimeric-protein lacks ADP ribosylation activity and comprises: (a) the PE translocation domain or a portion of the PE translocation domain sufficient to effect translocation of the chimeric protein to a cell cytosol; and (b) a portion of the endoplasmic reticulum retention domain sufficient to translocate the chimeric protein from endosome to endoplasmic reticulum; and wherein more than one Type IV pilin loop sequence is located between the portion of the PE translocation domain and the portion of the PE endoplasmic reticulum retention domain.

6. A composition comprising a chimeric protein of claim 5 and a pharmaceutically acceptable carrier.

7. A composition comprising a chimeric protein, the chimeric protein comprising: a non-toxic *Pseudomonas* exotoxin A (PE) sequence and a Type IV pilin loop sequence, the Type IV pilin loop sequence being located within the PE sequence, wherein the chimeric protein lacks ADP ribosylation activity and comprises: (a) the PE translocation domain or a portion of the PE translocation domain sufficient to effect translocation of the chimeric protein to a cell cytosol; and (b) a portion of the endoplasmic reticulum retention domain sufficient to translocate the chimeric protein from endosome to endoplasmic reticulum; and wherein the pilin loop sequence is located between the portion of the PE translocation domain and the portion of the PE endoplasmic reticulum retention domain and wherein the composition is formulated for nasal or oral administration.

8. The composition of claim 7, wherein the chimeric protein, when introduced into the host, is capable of generating polyclonal antisera that neutralize cytotoxicity of *Pseudomonas* exotoxin A.

9. The composition of claim 7, wherein the composition further comprises a pharmacologically acceptable carrier.

10. The composition of claim 7, wherein the chimeric protein further comprises a cell recognition domain that functions as a ligand for a cell surface receptor and that mediates binding of the chimeric protein to a cell.

11. The composition of claim 10, wherein the Type IV pilin loop sequence is a *Pseudomonas aeruginosa* Type IV pilin loop sequence.

12. The composition of claim 7, wherein the PE translocation domain consists of the amino acid sequence of positions 253–364 of SEQ ID NO:2 and the endoplasmic reticulum retention domain comprises the amino acid sequence of SEQ ID NO:21, SEQ ID NO:22, or SEQ ID NO:23.

13. The composition of claim 12, wherein the Type IV pilin loop sequence comprises the amino acid sequence of SEQ ID NO:3, SEQ ID NO:4, SEQ ID NO:5, SEQ ID NO:6, SEQ ID NO:7, SEQ ID NO:8, SEQ ID NO:9, or SEQ ID NO:10.

* * * * *